US008010296B2

(12) United States Patent
Loo et al.

(10) Patent No.: US 8,010,296 B2
(45) Date of Patent: Aug. 30, 2011

(54) APPARATUS AND METHOD FOR REMOVING NON-DISCRIMINATORY INDICES OF AN INDEXED DATASET

(75) Inventors: Lit-Hsin Loo, Dallas, TX (US); Leonid Hrebien, Valley Forge, PA (US); Moshe Kam, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 1520 days.

(21) Appl. No.: 10/538,390

(22) PCT Filed: Dec. 18, 2003

(86) PCT No.: PCT/US03/40677
§ 371 (c)(1),
(2), (4) Date: May 2, 2006

(87) PCT Pub. No.: WO2004/057524
PCT Pub. Date: Jul. 8, 2004

(65) Prior Publication Data
US 2007/0009160 A1    Jan. 11, 2007

Related U.S. Application Data

(60) Provisional application No. 60/435,067, filed on Dec. 19, 2002, provisional application No. 60/442,878, filed on Jan. 27, 2003.

(51) Int. Cl.
*G06F 19/00* (2011.01)
*G06F 17/10* (2006.01)
*G01N 24/00* (2006.01)
*B01D 59/44* (2006.01)

(52) U.S. Cl. ............... 702/19; 436/173; 250/281; 703/2

(58) Field of Classification Search ...................... None
See application file for complete search history.

(56) References Cited

U.S. PATENT DOCUMENTS

| | | | | |
|---|---|---|---|---|
| 5,794,185 A | * | 8/1998 | Bergstrom et al. | ........... 704/223 |
| 6,064,770 A | * | 5/2000 | Scarth et al. | ................... 382/225 |
| 7,027,933 B2 | * | 4/2006 | Paulse et al. | ..................... 702/27 |

OTHER PUBLICATIONS

Loo, Lit-Hsin et al., "Common Characteristics and Noise Filtering and Its Application in a Proteomic Pattern Recognition System for Cancer Detection," Proceedings of the 25th Annual International Conference of the IEEE EMBS, Sep. 17-21, 2003, pp. 2897-2900.
Petricoin III, Emanual F. et al., "Use of Proteomic Patterns in Serum to Identify Ovarian Cancer," The Lancet, 2002, pp. 572-575, vol. 359.
Petricoin III, Emanuel F. et al., "Serum Proteomic Patterns for Detection of Prostate Cancer," Journal of the National Cancer Institute, 2002, pp. 1576-1578, vol. 94, No. 20.
Loo, Lit-Hsin et al., "New Filter-Based Feature Selection Criteria for Identifying Differentially Expressed Genes," Proceedings of the Fourth International Conference on Machine Learning and Applications, IEEE, 2005, pp. 1-10.
Adam, Bao-Ling et al., "Serum Protein Fingerprinting Coupled with a Pattern-Matching Algorithm Distinguishes Prostate Cancer from Benign Prostate Hyperplasia and Healthy Men," Cancer Research, 2002, pp. 3609-3614, vol. 62.
Li, Jinong et al., "Proteomics and Bioinformatics Approaches for Identification of Serum Biomarkers to Detect Breast Cancer," Clinical Chemistry, 2002, pp. 1296-1304, vol. 48, No. 8.

* cited by examiner

*Primary Examiner* — Lori A Clow
(74) *Attorney, Agent, or Firm* — Knoble Yoshida & Dunleavy, LLC

(57) ABSTRACT

The present invention provides a device and method for removing non-discriminatory indices of an indexed dataset using ensemble statistics analysis. The device may include a data removal module (320) for removing non-discriminatory indices. For example, the data removal module (320) may comprise a common characteristic removal module and/or a noise removal module. In addition, the data analyzer (300) may comprise a normalization means (310) for normalizing the indexed data. The method of the present invention comprises the steps of identifying and removing portions of the set of data having insufficient discriminatory power based on ensemble statistics of the set of indexed data. For example, the method may include the steps of identifying and removing common characteristics and/or noise portions of the set of indexed data. In addition, the method may comprise the step of normalizing the indexed data either prior to or after the step of removing portions of the set of data.

7 Claims, 13 Drawing Sheets

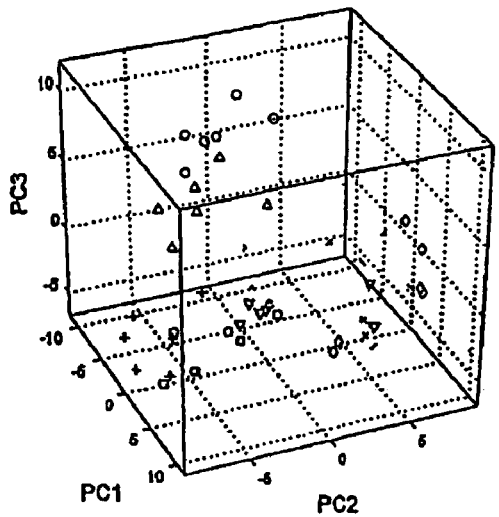
FIG. 8g
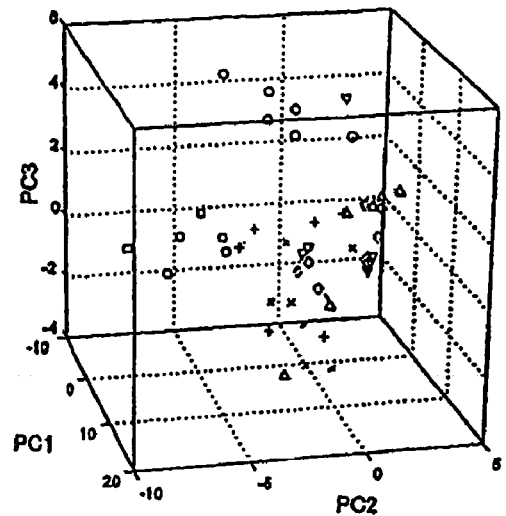
FIG. 8h
| | |
|---|---|
| × | Animal 1 (Group 1) |
| ◊ | Animal 2 (Group 1) |
| + | Animal 3 (Group 2) |
| □ | Animal 4 (Group 2) |
| △ | Animal 5 (Group 3) |
| ▽ | Animal 6 (Group 3) |
| ○ | Animal 7 (Group 4) |
FIG. 8i

APPARATUS AND METHOD FOR REMOVING NON-DISCRIMINATORY INDICES OF AN INDEXED DATASET

RELATED APPLICATIONS

This application is a National Stage of International Application No. PCT/US03/40677, filed Dec. 18, 2003, which claims the benefit of priority of U.S. Provisional Application 60/435,067, filed on Dec. 19, 2002 and 60/442,878 filed on Jan. 27, 2003, the entire contents of which application(s) are incorporated herein by reference.

BACKGROUND OF THE INVENTION

The term "indexed data" or "spectrum" refers to a collection of measured values called responses. Each response may or may not be related to one or more of its neighbor elements. When a unique index, either one-dimensional or multi-dimensional, is assigned to each response, the data are considered to be indexed. The index values represent values of a physical parameter such as time, distance, frequency, mass, weight or category. For index values that are measurable, the distance between consecutive index values (interval) can be uniform or non-uniform. Besides that, the indices of different indexed data might be assigned at standard or non-standard values. The response of the indexed data can include but are not limited to signal intensity, item counts, or concentration measurements. By way of example, the present invention is applicable to any of the aforementioned type of spectra.

Indexed data are used in a variety of pattern recognition applications. In general, the purpose of those pattern recognition applications is to distinguish indexed data that are collected from samples from subjects experiencing different external circumstances or influences; undergoing different internal modes or states; or originating from different species or types. The subjects include, but are not limited to, substances, compounds, cells, tissues, living organisms, physical phenomena, and chemical reactions. As used herein, the term "conditions" refers generally to such circumstances, influences, modes, states, species, types or combinations thereof The conditions are usually application-dependent. The underlying rationale of a pattern recognition application is that a response at each index may react differently to different conditions. If a response increases with the existence of a condition, the condition "upregulates" the response; if a response decreases with the absence of a condition, the process "downregulates" the response. Typically a collected spectrum comprises at least (1) the responses of interest, which are correlated to the conditions of interest; and (2) common characteristics and noise, which are uncorrelated to the conditions of interest, but which may be correlated to other conditions of non-interest.

In such applications of indexed data, a set of indexed data is usually collected under different conditions, thus forming an "indexed dataset". Within the dataset a category is a set of labels that represent a condition or a combination of conditions. The separation of indexed data from the indexed dataset into categories is usually performed by a pattern recognition system. In this regard the end-to-end objective of a pattern recognition system is to associate an unlabeled spectrum sample with one of several pre-specified categories ('hard' clustering), or alternatively to compute a degree of membership of the sample to each one of the categories ('soft' clustering).

However, present pattern recognition systems include a normalization module that is a major bottle neck. The normalization module is a bottle neck, because the amount of information that a feature extraction module can extract is limited by the amount of information that is retained by the normalization module. The performance degradation due to error in the normalization module often cannot be corrected by subsequent modules. Consequently, present pattern recognition systems suffer from a variety of deficiencies, which include lower processing speed and lower discriminatory-power than desired or, in certain instances, needed.

Applicants have discovered that one source of these deficiencies is the failure to remove the common characteristics and noise before normalization. Consequently in many applications where the interested response is weaker than the common characteristics, normalization to the common characteristics instead of the interested response reduces the discriminatory power of the spectra significantly. In addition, the large dimension of common characteristics and noise retained after normalization put extra burden on a feature extraction module and lower the processing speed of the pattern recognizer significantly. Accordingly, there is a need for removal of non-discriminatory indices before the feature extraction module, to permit increased discriminatory power, while minimiing the computational cost of the pattern recognition system.

FIELD OF THE INVENTION

The present invention relates generally to analyzing an indexed dataset and more specifically to methods, processes and instruments for performing methods of identifing and removing non-discriminatory indices in indexed dataset. As such, the invention is particularly pertinent to pattern recognition systems using an indexed dataset.

STATEMENT OF THE INVENTION

To address the above-stated needs, a data analyzer for use with a pattern classifier is provided to compress a set of indexed data. The data analyzer comprises a data removal module for identifyig and removing portions of the set of indexed data having insufficient discriminatory power based on the ensemble statistics of the set of indexed data. The data removal module functions to remove portions of the spectra from further processing if such portions do not have sufficient discriminatory power (namely if they cannot help classify the spectrum into an appropriate category). In this regard, the data removal module may comprise a common characteristic removal module which includes means for identifying and removing common characteristics of the set of indexed data based on the ensemble statistics of the set of indexed data. Alternatively or additionally, the data removal module may comprise a noise removal module which includes means for identifWing and removing noise portions of the set of indexed databased on ensemble statistics of the set of indexed data. In addition, the data analyzer may comprise a normalization means for normalzing the indexed data The normalization means may be configured to process the indexed data prior to or after the processing by the data removal module. Further, the data analyzer may include a feature extraction module for extracting a feature portion from the compressed indexed data to provide a set of feature indexed data and may include a classification module for classifying the feature indexed data to provide pattern classification of the set of indexed data.

The present invention also provides a method for analyzing a set of indexed data to compress the set of data. The method comprises the steps of identifyig and removing portions of the set of data having insufficient discriminatory power based on ensemble statistics of the set of indexed data, thereby providing a set of compressed indexed data. The method may include the steps identifyig and removing common characteristics of the set of data based on ensemble statistics of the set of indexed data. Alternatively or additionally, method may include the steps of identifyg and removing noise portions of the set of indexed data based on ensemble statistics of the set of indexed data. In addition, the method may comprise the step of normalizing the indexed data either prior to or after the step of removing portions of the set of data Further, the method may include the steps of extracting a feature portion from the compressed indexed data to provide a set of feature indexed data and classifying the feature indexed data to provide pattern classification of the set of indexed data

BRIEF DESCRIPTION OF THE DRAWINGS

The foregoing summary and the following detailed description of the preferred embodiments of the present invention will be best understood when read in conjunction with the appended drawings, in which:

FIGS. 8A-8I schematically illustrate the first three principal components that iesult from the analysis performed by each of the eight modules;

DETAILED DESCRIPTION OF THE INVENTION

Figure 1:
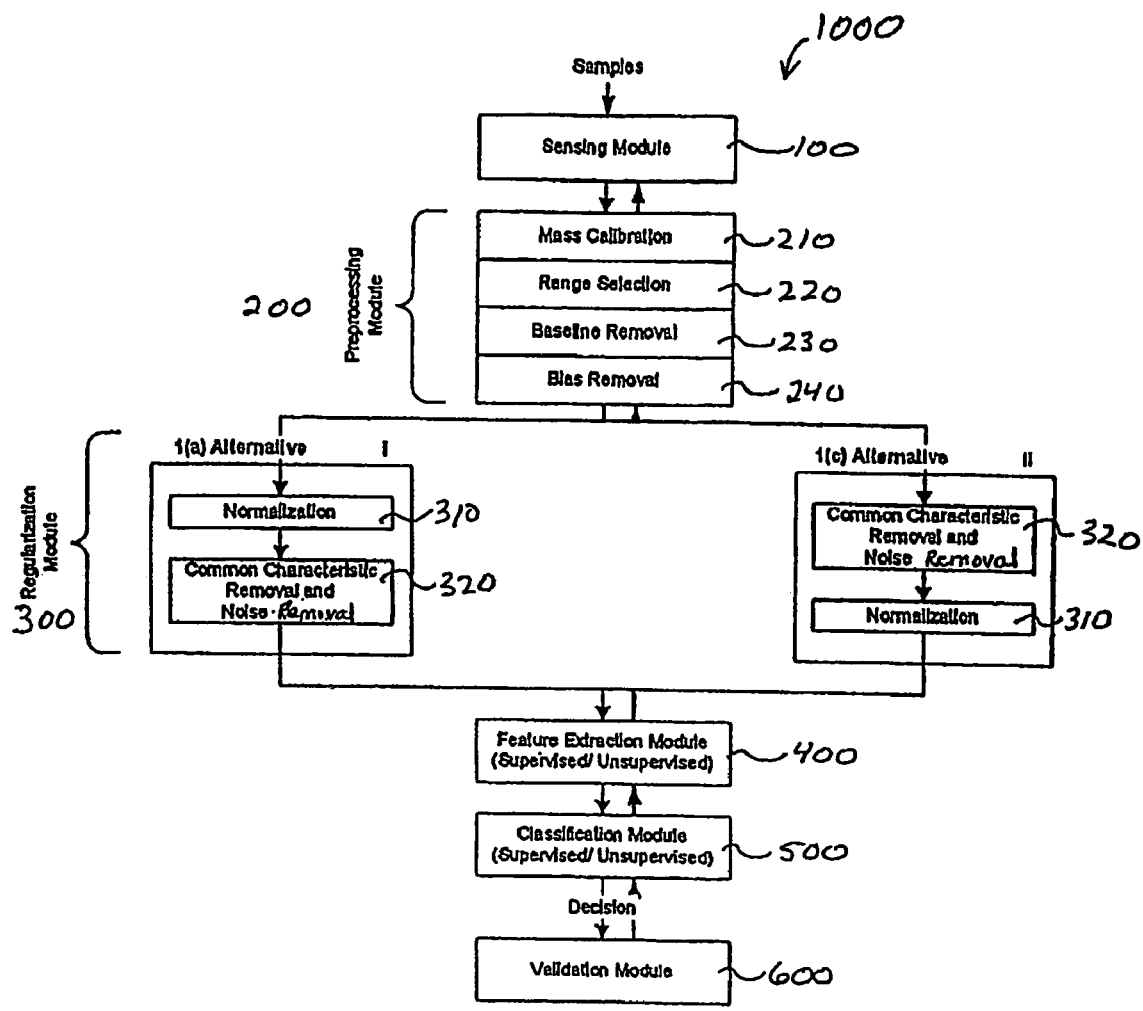
FIG. 1 schematically illustrates a proteomic pattern classifier in accordance with the present invention for classification of protein spectra.

Referring now to the figures, wherein like elements are numbered alike throughout, and in particular FIG. 1, aproteomic pattern classifier 1000 for classification of protein spectra is illustrated. The pattern classifier 1000 operates on spectra that may be collected by a variety of techniques. For example, the protein spectra may be provided by a Protein-Chip Biology System by Ciphergen Biosystems which provides a rapid, medium to high throughput analysis tool of polypeptide profiles (small proteins and polypeptides <20 kDa). The ProteinChip platform uses surface enhanced laser desorption/ionization time-of-flight mass spectrometry (SELDI-ToF-MS), which is a variant of matrix assisted laser desorption/ionization time-of-flight mass spectrometry (lM-LALDI-ToF-MS), to provide a direct readout of polypeptide profiles from cells and tissues. By selecting different Protein-Chip surface chemistries (e.g., hydrophobic, ion exchange, or antibody affinity), different polypeptide profiles can be generated. In addition to classification of SELDI-ToF-MS, the present invention has application to DNA microarray preprocessing analysis. Moreover, while the invention is described in an exemplary manner with application to classification of protein spectra, the present invention may also be used for the classification of other spectra.

The general structure ofthe pattern classifier 1000 is illustrated in FIG. 1 by a block diagram showing the various modules of the pattern classifier 1000. The proteomic pattern classifier 1000 includes a sensing module 100, which provides raw data to be analyzed and may include a time-of-flight detector. The raw data is provided to a preprocessing module 200 for converting the sensed raw signal (time-of-flight measurement) into a more manageable form (mass spectrum). The preprocessing module 200 includes four stages, namely a mass calibration stage 210, a range selection stage 220, a baseline removal stage 230, and a bias removal stage 240, described more fully below.

A regularization module 300 is also provided to receive the spectra from the preprocessing module 200 and functions to standardize spectra that may have been obtained under different measurement conditions. The regularization module 300 may include two alternative paths, $1(a)$ and $1(c)$, each path having a normalization stage 310 and/or a common characteristic removal and noise removal stage 320. The common characteristic removal and noise removal stage 320 compresses the spectra by removing portions of the spectra that have less than a desired amount of discriminatory power. Downstream from the regularization module 300, afeature extraction module 400 is provided to compress the spectra generated by the regularization module 300 by extracting a vector of characteristics (features) that represent the data Ideally, spectra that belong to the same category would have features that are very similar in some distance measure, while spectra that belong to different categories would have features that are very dissimilar.

A classification module 500 is provided for associating each extracted feature vector with one (or several) of a pre-specified spectrum categories. The classification module 500 may utilize, for example, neural networks (e.g., a graded response multi-perceptron) or hierarchical clustering. The former are used when training data are available, the latter when such data are not available.

After the classification module 500, a validation module 600 may be provided to assess the performance of the system by comparing the classification result to the "ground truth" in labeled examples.

Preprocessing

Figure 2:
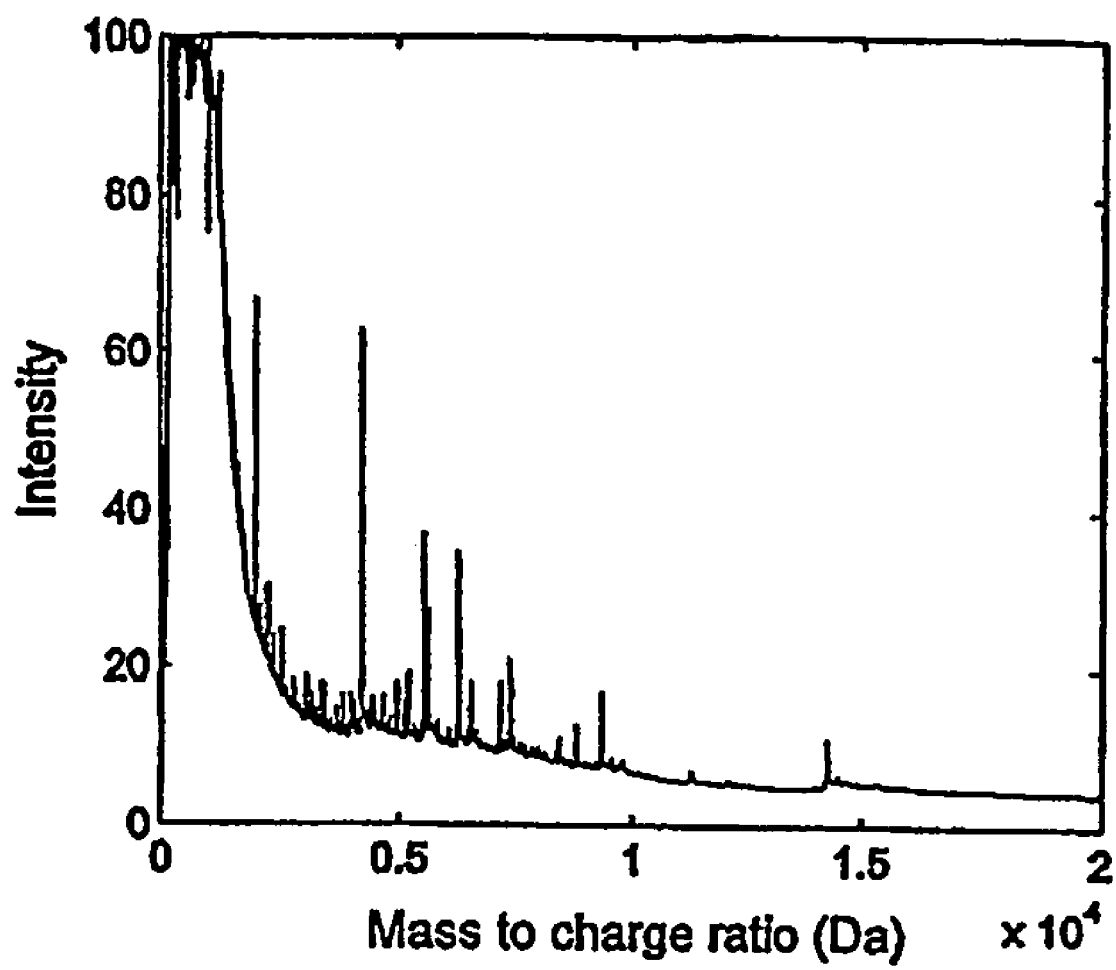
FIG. 2 illustrates a raw spectrum obtained from a rat liver.

Turning now in more detail to the preprocessing module 200, the operation of the preprocessing module 200, and in particular each of its four stages, is described. The mass calibration stage 210 assigns molecular weights to the raw time of flight (ToF) data supplied from the sensing module 100. Typically this process involves acquiring a spectrum from a standard with at least five peptides of various molecular weights. Following that, a quadratic equation, which relates the ToF to molecular weight, is fit to the ToF values ofthe standard peaks in the spectrum. The generated equation can then be used to convert raw ToF data, which are collected under the same instrumental conditions (e.g. laser intensity, time of collection, focusing mass, and time lag), to raw polypeptide mass spectra. The obtained spectra are described in terms of their intensity, as measured on the mass spectrometer, versus molecular weight (in units of mass-to-charge ratio). The graphs of intensity vs. molecular weight are discretized along the horizontal axis. For example, a raw spectrum obtained from a rat liver is shown in FIG. 2. The mass calibration stage 210 may conveniently be performed on the data collection system, e.g., ProteinChip Biology System.

Following the processing by the mass calibration stage 210, the range selection stage 220 is used to discard spectrum intervals that contain little discriminatory information. Depending on the experimental configurations and sample types, some intervals of molecular weights in the spectrum may be dropped, because such intervals prove to be noisy and unreliable. These intervals may include areas where most of the signal is due to the matrix molecules.

After the range selection stage 220, the baseline removal stage 230 processes the spectra from the range selection stage 220 to eliminate the baseline signal caused by chemical noise from matrix molecules added during the SELDI process. The baseline removal should not affect the discriminatory information sought.

Figure 3:
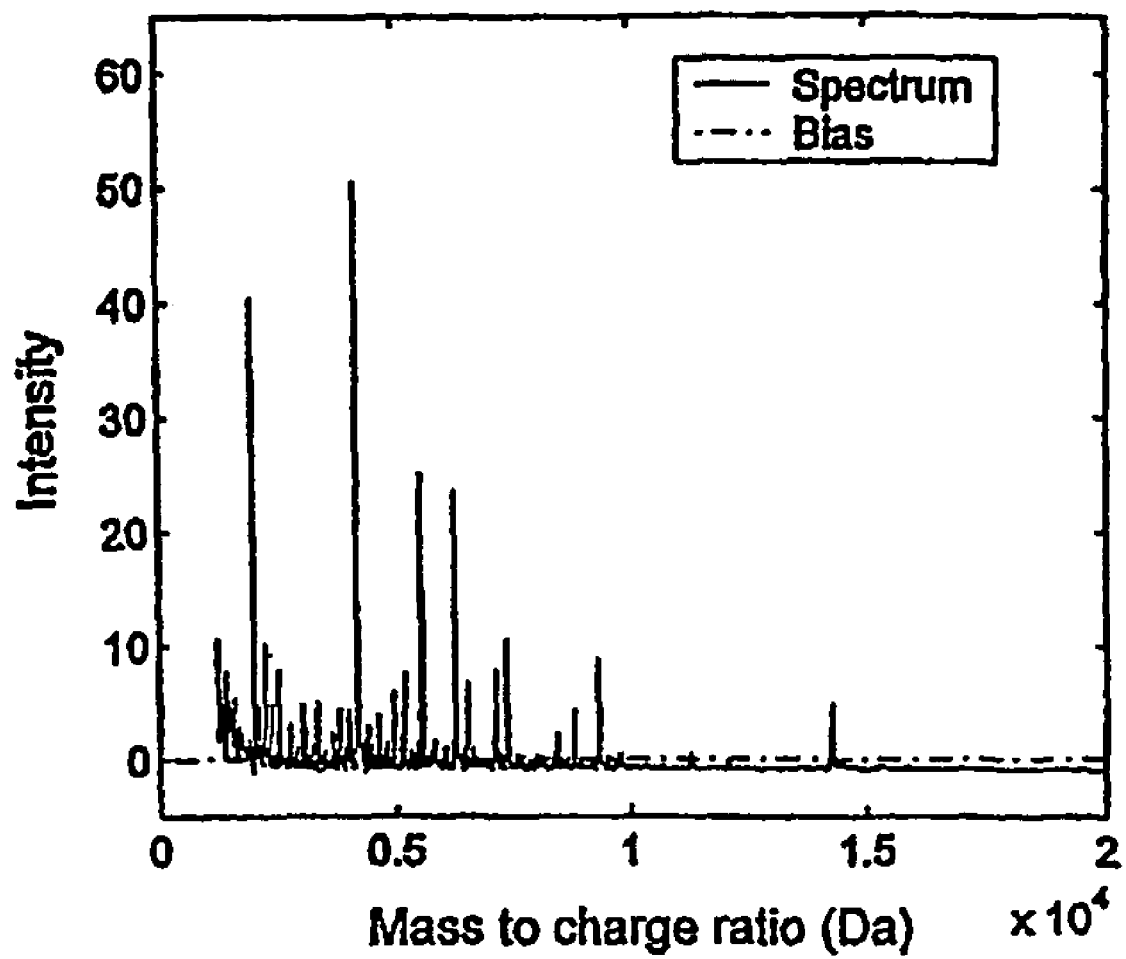
FIG. 3 schematically illustrates the processed spectrum of FIG. 2 after processing by the preprocessing module.

For the examples provided herein, baseline removal was performed by parsing the spectral domain into consecutive intervals of 100 Da The lowest point (local minimum) in each interval was determined, and a virtual baseline was created by fitting a cubic spline curve to the local minima The virtual baseline was then subtracted from the actual spectrum. The result was a spectrum with a baseline hovering above zero. In addition, the spectra were transformed to have a zero mean by subtracting the mean of the spectra from each sampled point at the bias removal stage 240. An example of the preprocessed spectra up to and including the bias removal stage 240, corresponding to the raw spectra in FIG. 2, is shown in FIG. 3. The segment before 1.25 kDawas dropped. The preprocessed zero-mean and "flat" baseline spectra is referred to herein as the "polypeptide spectra".

The polypeptide spectra are passed to the regularization module 300 to normalize the data and to remove common characteristics and noise that have an undesirably low amount of discriminatory power. Before proceeding with a description of the regularization module 300, the mathematical model of the present invention is presented, because the model provides the basis for the design of the two stages of the regularization module 300.

Mathematical Model for Protein Spectrum Measurement

In accordance with the present invention, a mathematical model for the preprocessed polypeptide spectra is provided. The model reflects the observation that polypeptide spectra are often contaminated by a "common characteristic" signal whose variations are not correlated to the protein response of interest. The noise-free protein expression of a collected biological sample (e.g., biofluids, cells, tissues) from a "normal" subject is modeled as a common characteristic, denoted $C[m]$. (As used herein, capital letters represent stochastic processes, bold lowercase letters represent random variables, non-bold capital letters represent constants, and non-bold lowercase letters represent deterministic variables.)

$C[m]$ is a non-negative stochastic process whose values are known for a particular realization at discrete values of the molecular weights (m). The definition of "normal" is study-dependent. For example, the control group of a study, to which no condition was applied, may be "normal". In the examples and description that follow, the normal subject is selected to be a control group.

In the presence of a certain condition (g), the noise-free total protein expression of a sample is modeled as $C[m]+A_g[m]$, where $A_g[m]$ is an additive component representing the response to condition g. The condition, $g \in \{1, 2, \ldots, G\}$, is a label representing a single process (or a combination of processes), such as a disease-associated or toxin-induced biochemical processes, where G different conditions may be present in a study. $A_g[m]$ can have both positive (upregulation) and negative (downregulation) values. The condition $g=0$ is selected to represent the null response of the control group, ie. $A_0[m]=0$. As used herein, the term group is applied to all samples subject to the same condition. The SELDI process, which obtains the protein profile of the samples incubated on a ProteinChip, corresponds to an experiment.

Let $\hat{A}_{g,n}[n]$ be the preprocessed polypeptide spectrum observed during the n-th experiment (such as the one in FIG. 3). $\hat{A}_{g,n}[m]$ is modeled as $$\hat{A}_{g,n}[m] = \alpha_n[A_g[m] + C[m]] + N_n[m], \quad (1)$$

where $N_n[m]$ is an additive noise term introduced by the experiment; and $\alpha_n$ is a molecular-weight independent attenuation coefficient, accounting for the varying amount of protein ionized by the ionizer and detected by the spectrometer collector across experiments. $\alpha_n$ is experiment-dependent and assumes a value between 0 and 1.

To simplify notation, the explicit dependency on m from the equations is dropped when the dependency is clear from context.

The model includes an assumption that $\alpha_n$, $A_g$, C and $N_n$ are statistically independent (indeed, the physical processes that created these signals are independent). $A_g$, C and $N_n$ are discrete stochastic processes and, in general, non-stationary. Each experiment (spectrum) is a particular realization of the process, and a collection of spectra constitutes an ensemble. In the equations that follow, the context indicates whether molecular weight statistics (for a spectrum) or with ensemble statistics (across a set of spectra) are indicated. In particular, the subscript n (for the $n^{th}$ experiment) is used when calculating molecular weight statistics (e.g., $E_n\{C\}$), as opposed to ensemble statistics (e.g., $E\{C[m]\}$.)

Since the non-zero bias of a spectrum has been removed during operation of the preprocessing module 200, $E_n\{\hat{A}_{g,n}\}=0$. Further, it is assumed that $E_n\{\alpha_n\}=\alpha_n$ because the attenuation in an experiment is typically independent of the molecular weight.

In order to compare spectra and create classes of spectra, a process for measuring the 'distance' between them is required. For example, the squared Euclidean distance may be used for that purpose, with vector multiplication carried out as a dot product.

The model may be understood by considering two experiments, $n=i,j$. Spectrum i is collected from a sample subject to conditions ($g=p$); spectrum j is collected from a sample subject to condition q ($g=q$). It is possible that $p=q$. The expected distance between spectra, using the squared Euclidean distance, is then $$\Delta D = E\{(\hat{A}_{p,i} - \hat{A}_{q,j})^2\}. \quad (2a)$$

In order to simplify the expansion of (2a), it is assumed that $A_g$ and C are usually much larger than $N_n$; therefore, the dot products ($N_n A_g$ and $N_n C$) yield values much smaller than $A_g C$ and can be ignored.

By definition, $A_g$ and C are not strongly correlated (or else C would be correlated to the condition g and no longer be a "common characteristic"). Thus, $E\{A_g C\}$ is much smaller than the autocorrelation of the same process (such as $E\{A_g^2\}$ or $E\{C^2\}$), and can be ignored as well. After expanding (2a), the expected distance between spectra can then be approximated to be $$\Delta D \cong E\{(\alpha_i A_p - \alpha_j A_q)^2 + (\alpha_i - \alpha_j)^2 C^2 + (N_i - N_j)^2\} \quad (2b)$$
$$= \Delta A + \Delta C + \Delta N$$
where
$$\Delta A = E\{(\alpha_i A_p - \alpha_j A_q)^2\} \quad (2c)$$
$$\Delta C = (\alpha_i - \alpha_j)^2 E\{C^2\} \text{ and}$$
$$\Delta N = E\{(N_i - N_j)^2\}$$

In terms of the theoretical model, the desired measurement is the distance between protein expressions under different condition, i.e. $\Delta A_0 = E\{(A_p - A_q)^2\}$. From expressions (2b,c) it is observed that the desired distance ($\Delta A_0$) is embedded in the measured distance ($\Delta D$). In practice, $\Delta D$ is measured, which contains the undesirable weights $\alpha_i$ and $\alpha_j$ in $\Delta A$ and the undesirable interference terms $\Delta C$ and $\Delta N$. In order to extract the desired distance, $\Delta A_0$, the effects of the interference terms $\Delta C$ and $\Delta N$ as well as the undesirable weights $\alpha_i$ and $\alpha_j$ should be reduced. Hence, a purpose of the regularization module 300, expressed in terms of the above model, is to eliminate or minimize the undesirable weights $\alpha_i$ and $\alpha_j$ in $\Delta A$ and the undesirable interference terms $\Delta C$ and $\Delta N$ in the regularization module 300, thus allowing the classification module 500 to measure $\Delta A_0$ as accurately as possible.

Regularization Module

Common Characteristic Removal and Noise Removal Stage

When, $\Delta C$ and $\Delta N$ in (2) are significantly larger than $\Delta A$, it would be beneficial to remove molecular weights which exhibit large values of $\Delta C$ and $\Delta N$ in order to extract the useful information from $\Delta D$ (namely, $\Delta A$, and $\Delta A_0$). The present invention removes such molecular weights through one or more variance analyses using ensemble statistics, followed by an additional, optional bias removal step as part of a common characteristic removal (first variance analysis) and noise removal (second variance analysis) stage 320. The noise removal portion of stage 320 may optionally be performed prior to the common characteristic removal portion of stage 320.

Common characteristics, by definition, are shared by both control and non-control samples. Thus, the control samples, which do not include other condition-specific characteristics, can be used to detect and remove these common characteristics. A key observation is that at molecular weights that correspond to significant common characteristics, there exists high variances across samples. Common characteristics with small variance have little effect on the subsequent classification module, since such characteristics would cancel each other when the distance between spectra is calculated. The observed spectrum for the control group is $\hat{A}_{0,n}[m] = \alpha_n C[m] + N_n[m]$, and the ensemble variance under the statistical independence assumptions is $$\sigma^2[m] = \text{var}(\alpha_n[m]C[m]) + \text{var}(N_n[m]), \quad (3)$$

where var( ) is the variance operator.

In practice, only few molecular weights exhibit significant values of $\text{var}(\alpha_n[m]C[m])$, and at these molecular weights these variations are much larger than the variations of the noise, namely, $\text{var}(\alpha_n[m]C[m]) \gg \text{var}(N_n C[m])$. Thus, portions of the spectrum where the ensemble variance $\sigma^2[m]$ is larger than a certain threshold can be filtered out (viz., remove molecular weights m that correspond to such spectrum portions). This threshold, $\sigma_{thres}^2$, is set to be $$\sigma_{thres}^2 = \lambda\{\max(\sigma^2[m]) - \min(\sigma^2[m])\} + \min(\sigma^2[m]), \quad (4)$$

where $0 < \lambda < 1$ may be chosen to have values between and 0.01 and 0.05 which can provide a good tradeoff between the need to remove molecular weights that correspond to high variance and the need not eliminate molecular weights where specific characteristics of the non-control samples may be expressed. While some useful information from $A_g[m]$ might fall into the eliminated molecular weights, the presence of $C[m]$ with strong variation at those values of m render these points useless anyway for discrimination between conditions. Thus, after the common characteristic removal portion of stage 320, the spectrum becomes $$\hat{A}_{g,n}[m] = \alpha_n [A_g[m] + C[m]] + N_n[m], \quad (5)$$

where the retained $C[m]$ are constant or close to constant across each molecular weight. Since $C[m]$ is independent of the condition g, equation (5) becomes $$\hat{A}_{g,n}[m] \alpha_n B_g[m] + N_n[m] \quad (6a)$$

where $$B_g[m] = A_g[m] + C[m]. \quad (6b)$$

A second variance analysis, the noise removal portion of stage 320, is used to eliminate additional portions of the spectra that correspond to other data with little discriminatory power. These data are characterized by relatively small variance across all spectra (control and non-control). These data correspond to a portion of the spectrum that are "noise only". By measuring the ensemble variance across all spectra $$\sigma^2[m] = \text{var}(\alpha_n[m]B_g[m]) + \text{var}(N_n[m]) \quad (7)$$
$$\cong \text{var}(\alpha_n[m]A_g[m]) + \text{var}(N_n[m]).$$

Based on the observation that the variance of noise is typically much smaller than the variance, an acceptable method for distinguishing between regions of "noise only" and regions of "signal plus noise" is given by $$\text{var}(\alpha_n B_g[m]) \gg \text{var}(N_n[m]). \quad (8)$$

Thus, the "noise only" portions of the spectrum can be eliminated by removing the molecular weights of index m where the ensemble variance $\sigma^2[m]$ falls below a threshold. Again, the threshold is of the form of equation (4). Values of $\lambda$ between 0.01 and 0.05 were found to provide a good tradeoff between the need to remove molecular weights, which correspond to little discriminatory information and the need to retain molecular weights where significant variations of the signal of interest, namely $A_g[m]$, are present.

After the second variance analysis (noise removal), the retained spectrum is still expressed by (6a,b). However, the spectrum now is now compressed to include a smaller number of molecular weights than the original spectrum. For example, in the examples that follow, a reduction in the cardinality of 60% to 98% of the original domain were obtained. The remaining values in retained spectrum correspond to molecular weights that have large variance across spectra obtained from all conditions, but relatively small variance across spectra from the control group. Although the additive noise $N_n[m]$ is still present in the compressed, retained spectrum, (namely at molecular weights where there are significant values of $A_g[m]$), the smaller domain reduces the contribution of the ΔN term in (2b) significantly. Since the smaller domain is now dominated by the peaks of $B_g[m]$, it is also safe to assume $$E_n\{\alpha_n B_g[m]\} \gg E_n\{N_n[m]\}. \tag{9}$$

After the common characteristic removal and noise removal stage 320, the retained spectrum may have a non-zero bias. Accordingly, an optional step of bias removal may be provided, which may be similar to the bias removal stage 240 performed during preprocessing. The bias is subtracted from the spectrum, and it becomes $$\hat{A}_{g,n}[m] = \alpha_n[B_g[m]] + N_n[m] - \mu_n, \tag{10a}$$

where $$\mu_n = E_n\{\alpha_n[B_g[m]] + N_n[m]\} \tag{10b}$$
$$= \alpha_n E_n\{B_g[m]\} + E_n\{N_n[m]\}.$$

Normalization to Standard Deviation

With the removal of common characteristics and noise, the dominant term in (2b) is ΔA, which differs from the desired $\Delta A_0$ due to the presence of the experiment-dependent attenuation coefficients $\alpha_n$ (see equation (1)). One way to reduce the effects of $\alpha_n$ is to normalize the observed spectrum to its standard deviation ($\sigma_n$) at the normalization stage 310.

The standard deviation is given by $$\sigma_n = \sqrt{E_n\{(\hat{A}_{g,n})^2\} - E_n^2\{\hat{A}_{g,n}\}} \tag{11a}$$
$$= \sqrt{E_n\{(\hat{A}_{g,n})^2\}}$$
$$= \sqrt{\alpha_n^2[E_n\{B_g^2\} - E_n^2\{B_g\}] + 2\alpha_n[E_n\{B_g N_n\} - E_n\{B_g\}E_n\{N_n\}] + [E_n\{N_n^2\} - E_n^2\{N_n\}]}$$

Under the assumption in (9), $$\sigma_n \cong \alpha_n \sqrt{E_n\{B_g^2\} - E_n^2\{B_g\}}. \tag{11b}$$

Following (8) and (9), the following relationship results $$E_n\{\alpha_n^2 B_g^2[m]\} - \alpha_n^2 E_n^2\{B_g[m]\} \gg E_n\{N_n^2[m]\} - E_n^2\{N_n[m]\}E_n \tag{12}$$
$$\{\alpha_n^2 B_g^2[m] - N_n^2[m]\} \gg \alpha_n^2 E_n^2\{B_g[m]\} - E_n^2\{N_n[m]\} \gg 0$$
$$\therefore E_n\{B_g^2[m]\} \gg \frac{E_n\{N_n^2[m]\}}{\alpha_n^2}.$$

By using (11) and (12), the square of the normalized expected distance can be simplified to The distance $\Delta\tilde{D}$ is analogous to the correlation coefficient between $B_p$ and $B_q$ (or between $A_p$ and $A_q$ since C[m] is constant across spectra). When $A_p$ and $A_q$ are highly uncorrelated (spectra are different), $\Delta\tilde{D} \to 2$; when $A_p$ and $A_q$ are highly correlated (spectra are close to each other), $\Delta\tilde{D} \to 0 \Delta\tilde{D}$. can thus be used as a statistical distance measurement between $A_p$ and $A_q$.

Had the common characteristics and noise not been removed before the normalization stage 310, the expression for the spectrum in (10a) would consist of a non-constant common characteristic term, which could "contaminate" the normalization in (13). Furthermore, assumption (11) on the negligibility of $N_n[m]$ might not be valid. For this reason, it may be desirable to introduce the common characteristics and noise removal stage 320 before the normalization stage 310, as illustrate as path 1c in FIG. 1, rather than introducing the common characteristics and noise removal stage 320 stage after the normalization stage 310 (path 1a).

As explained above, normalization to standard deviation may be preferred when the distance between spectra is measured through the squared Euclidean distance. However, other normalization schemes may be used with the present invention. For example, normalization may be made relative to the maximum value of the spectrum. If normalization to the maximum value is performed after the common characteristics and noise removal stage 320 and after the optional bias removal, an analogous expression to (13) would be $$\Delta\tilde{D} \cong E_n\left\{\left(\frac{\alpha_i B_p + N_i}{\alpha_i B_{p\,max}} - \frac{\alpha_j B_q + N_j}{\alpha_j B_{q\,max}}\right)^2\right\} \tag{14}$$
$$\cong E_n\left\{\left(\frac{B_p}{B_{p\,max}} - \frac{B_q}{B_{q\,max}}\right)^2\right\}$$

When $B_{p\,max}$ and $B_{q\,max}$ were close to each other, $\Delta\tilde{D}$ would be proportional to the square Euclidean distance between $B_p$ and $B_q$ (or $A_p$ and $A_q$), as desired. However this condition may not hold in practice, in which case $\Delta\tilde{D}$ can be distorted severely from $B_p$-$B_q$ by $B_{p\,max}$ and $B_{q\,max}$. Hence, normalization to the maximum may not be desirable in such applications, in which case normalization to the standard deviation may be preferable.

As an additional alternative normalization scheme, normalization may be made to the total ion current. Due to the assumptions made by a total ion current scheme (as described below), this normalization scheme may best be applied to spectra that have not first been filtered to remove noise and common characteristics. During a first step of the normalization, the total ion current, or the "total area under the curve", is calculated and divided by the number of points where it was calculated (thus providing the average ion current). To sim- $$\Delta\tilde{D} \cong E_n\left\{\left(\frac{\alpha_i B_p + N_i}{\sigma_i} - \frac{\alpha_j B_q + N_j}{\sigma_j}\right)^2\right\} \tag{13}$$
$$= E_n\left\{\frac{\sigma_j^2 \alpha_i^2 B_p^2 - 2\sigma_i \sigma_j \alpha_i \alpha_j B_p B_q + \sigma_i^2 \alpha_j^2 B_q^2 + \sigma_j^2 N_i^2 - 2\sigma_i \sigma_j N_i N_j + \sigma_i^2 N_j^2}{\sigma_i^2 \sigma_j^2}\right\}$$
$$\cong E_n\left\{-2\frac{B_p B_q}{\sqrt{E\{B_p^2 + \left(\frac{N_i}{\alpha_i}\right)^2\}} \sqrt{E\{B_q^2 + \left(\frac{N_j}{\alpha_j}\right)^2\}}} + \frac{B_p^2}{E\{B_p^2 + \left(\frac{N_i}{\alpha_i}\right)^2\}} + \frac{B_q^2}{E\{B_p^2 + \left(\frac{N_j}{\alpha_j}\right)^2\}}\right\}$$
$$\cong 2 - 2E_n\left\{\frac{B_p B_q}{\sqrt{E\{B_p^2\}} \sqrt{E\{B_q^2\}}}\right\}$$

plify the analysis, it is assumed that the intensity of a spectrum is relatively constant within a small molecular mass interval, say 1 Da The assumption is verified by observation of several hundred actual polypeptide spectra. In this case, the average ion current is $$\bar{I}_n = \frac{1}{M}\sum_m \hat{A}_{g,n}[m] = \frac{1}{M}\sum_m \alpha_n(A_g[m] + C[m]) + N_n[m], \quad (15)$$

where M is the total number of molecular weight indices.

During a second step of normalization, the overall average ion current ($E\{\bar{I}_n\}$) is calculated. Finally, each spectrum is multiplied by a factor, which is equal to the overall average ion current divided by average ion current for that spectrum, namely $E\{\bar{I}_n\}/\bar{I}_n$. The normalized spectrum becomes $$\tilde{A}_{g,n}[m] = \{\alpha_n(A_g[m] + C[m]) + N_n[m]\}\frac{E\{\bar{I}_n\}}{\bar{I}_n} \quad (16)$$

$$= \beta \frac{A_g[m] + C[m] + \frac{N_n[m]}{\alpha_n}}{\sum_m \left(A_g[m] + C[m] + \frac{N_n[m]}{\alpha_n}\right)}$$

where $$\beta = E\left\{\alpha_n \sum_m \left(A_g[m] + C[m] + \frac{N_n[m]}{\alpha_n}\right)\right\}$$

is a constant factor for a particular study (set of experiments). When substituting (16) into the expected distance measurement, the distance measurement is scaled by $$\sum_m \left(A_g[m] + C[m] + \frac{N_n[m]}{\alpha_n}\right). \quad (17)$$

If the expression in (17) is relatively constant across spectra, this normalization scheme is able to provide a good distance measurement between $A_p$ and $A_q$.

Alternative Reaularization Modules

Figure 4:
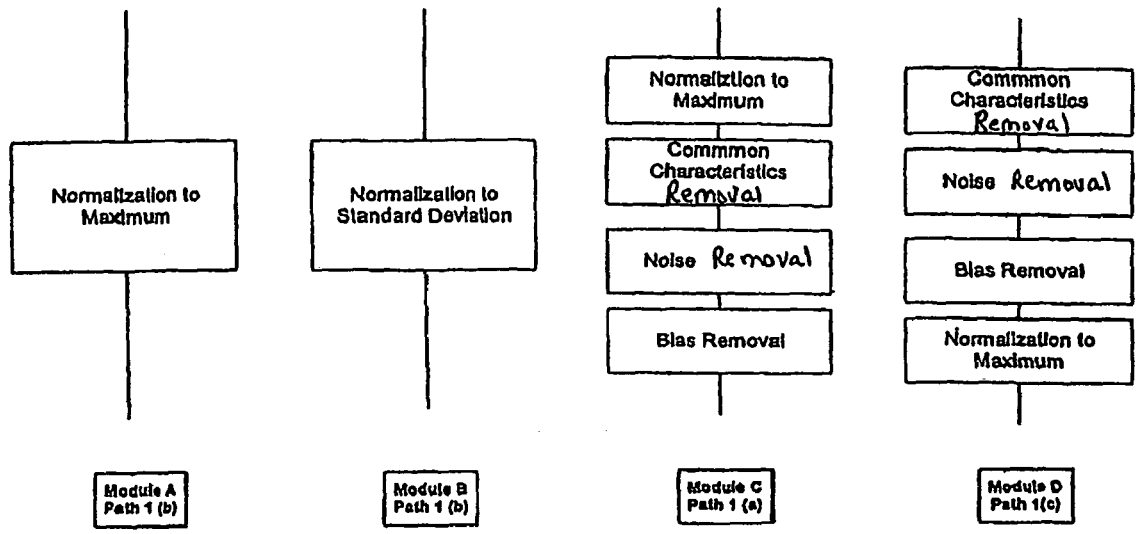
FIG. 4 schematically illustrates eight alternatives for a regularization module in accordance with the present invention.
Figure 4:
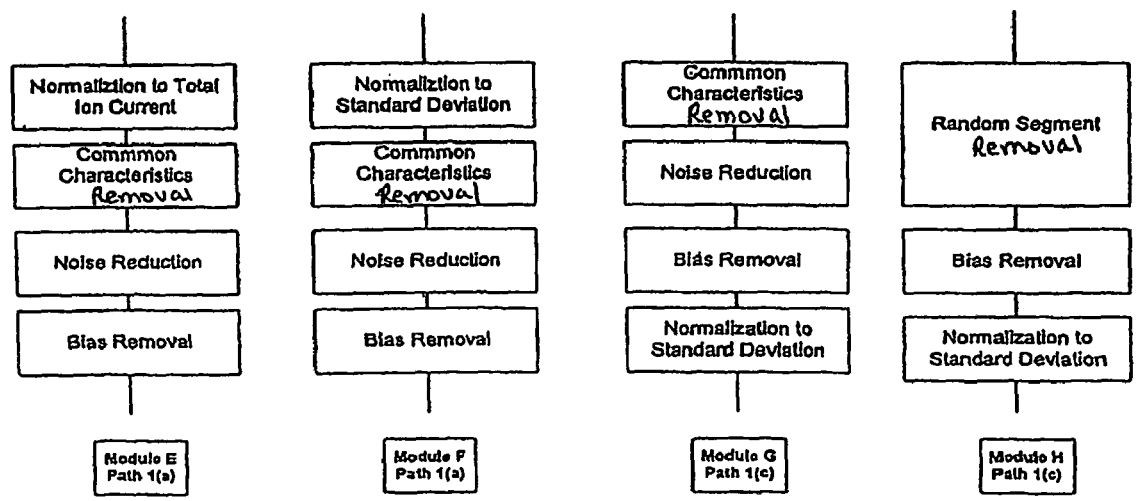

In view ofthe various alternatives that may be utilized within the regularization module 300, several different regularization module 300 schemes maybe provided from selective use of such alternatives. For example, eight different alternatives for the regularization module 300 are illustrated in FIG. 4 and snmmarized in Table 1.

Modules A and B represent a regularization module 300 that performs normalization only. In Module A the normalization is to the maximum. In Module B, normalization is to the standard deviation.

Modules C and D are two variations involving normalization to the maximum. In Module C the normalization to the maximum precedes common characteristic and noise removal. In Module D the common characteristic and noise removal precedes the normalization.

Module E uses normalization to total ion current, followed by common characteristic and noise removal.

Modules F and G are two variations involving normalization to the standard deviation. In Module F the normalization precedes common characteristic and noise removal. In Module G the common characteristic and noise removal precedes the normalization.

Module H is a variation of module G. Instead of performing common characteristic removal and bias removal, Module H removes from the input a randomly-selected segment, equal in size to the segment removed by the common characteristic and noise removal stage ofmodule G. The purpose ofintroducing Module H is to examine whether the improvements observed using Module G are solely due to data set reduction. In each of modules C-H, the bias removal and normalization steps are optional.

TABLE I

Alternative Regularization Modules

Module A (Normalization only - path 1b)
   A1. normalization to maximum
Module B (Normalization only - path 1b)
   B1. normalization to standard deviation
Module C (Normalization before Filtering - path 1a)
   C1. normalization to maximum
   C2. common characteristics reduction
   C3. noise reduction
   C4. bias removal
Module D (Filtering before Normalization - path 1c)
   D1. common characteristics reduction
   D2. noise reduction
   D3. bias removal
   D4. normalization to maximum
Module E (Normalization before Filtering - path 1a)
   E1. normalization to total ion current
   E2. common characteristics reduction
   E3. noise reduction
   E4. bias removal
Module F (Normalization before Filtering - path 1a)
   F1. normalization to standard deviation
   F2. common characteristics reduction
   F3. noise reduction
   F4. bias removal
Module G (Filtering before Normalization - path 1c)
   G1. common characteristic reduction
   G2. noise reduction
   G3. bias removal
   G4. normalization to standard deviation
Module H (Filtering before Normalization - path 1c)
   H1. segment removal
   H2. bias removal
   H3. normalization to standard deviation Feature Extraction Returning now to FIG. 1, after the regularization module-300, thefeature extraction module 400 is provided to compress the spectrum further by extracting a vector of characteristics (features). A variety of techniques may be used by the feature extraction module 300. For example, the feature extraction module 300 may utilize principal component analysis (PCA) or genetic algorithms (GA). Principal component analysis may desirablybe used when no taining information is available, and genetic algorithms may be used otherwise.

Principal component analysis is used to reduce the order of high dimensional data to a smaller set of principal components (C). Each principal component is a linear combination of the original data that exhibits the maximum possible variance. All the principal components are orthogonal to each other so there is no redundant information. The principal components form an orthogonal basis for the space of the data.

Figure 5:
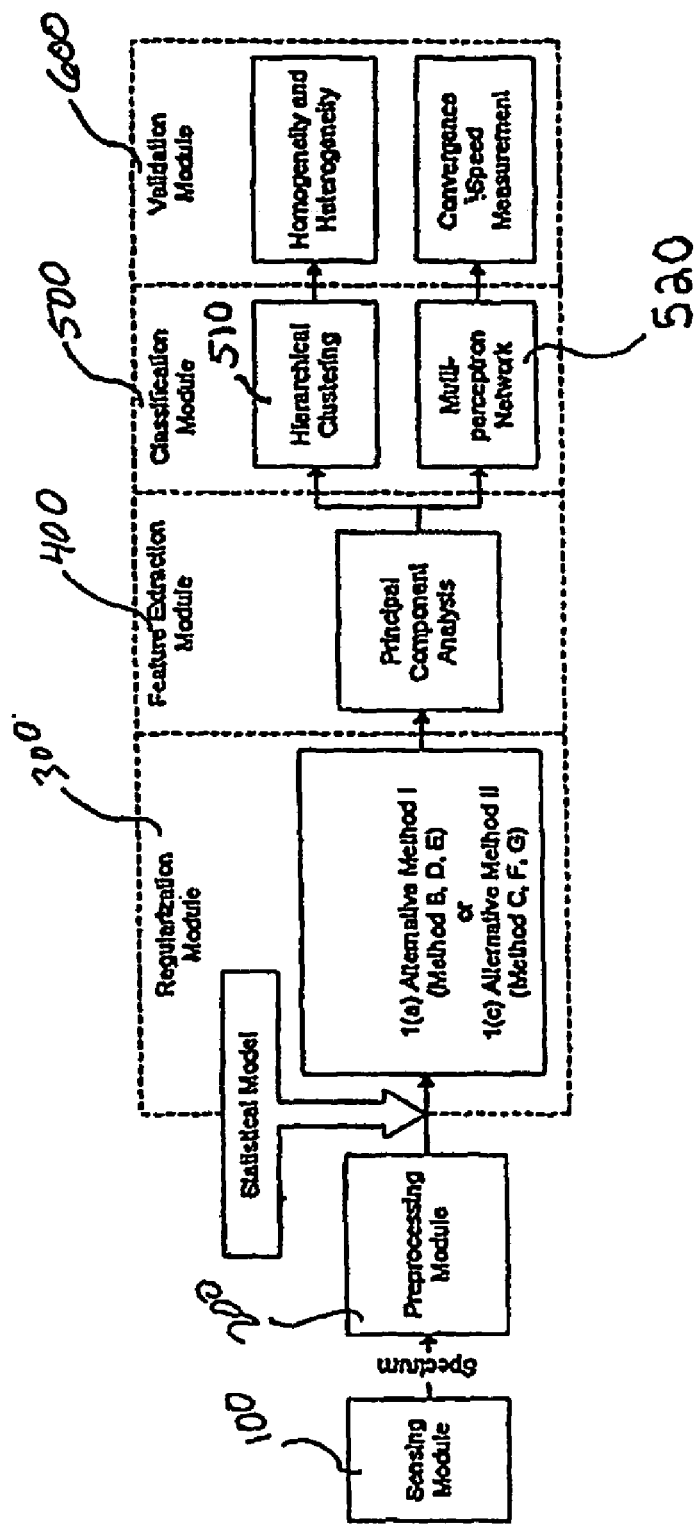
FIG. 5 schematically illustrates a proteomic pattern classifier in accordance with the present invention that incorporates principal component analysis.

The principal components are usually listed in an ascending variance order (PC1 having the largest variance). Then, the cumulative percentage of total variability is calculated for each principal component and all principal components preceding it on the list. The ordered set of principal components that cumulatively express a certain percentage of total variability (such as 90%) is extracted to serve as the feature set. In addition, principal component analysis can provide a (3D) visual representation of the original high dimensional data, which often preserves the relative distance between neighborhood samples. By viewing this projection of the data, one can get an appreciation for the distance between classes of spectra, which are related to the homogeneity and heterogeneity of the clusters. FIG. 5 shows a proteomic pattern classifier 1000 in accordance with the present invention that incorporates principal component analysis in thefeature extraction module 400. Thefeature extraction module 400 extracts the principal components from the (compressed and normalized) output of the regularization module 300.

Figure 6:
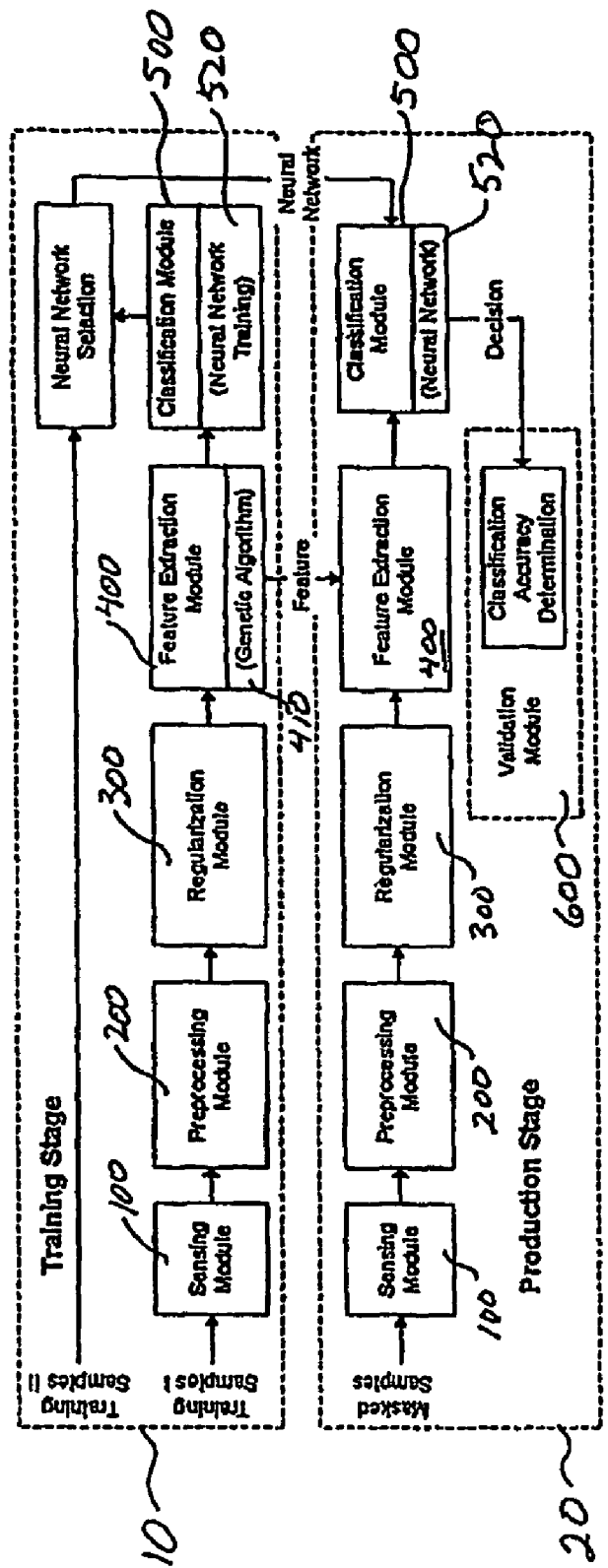
FIG. 6 schematically illustrates a proteomic pattern classifier in accordance with the present invention that incorporates a supervised feature extraction module.

Alternatively, if a training set is available, a supervisedfeature extraction module 400 can be used to detect and remove points that have little discriminatory power, as illustrated in FIG. 6. Feature extraction in this case is an optimization problem whose objective is to find a combination of molecular weights (features) that yield the best classification performance under a given classification algorithm. This kind of optimization problem may be approached through stochastic search methods, such as a genetic algorithm 410.

The genetic algorithm 410 searches the solution space of the optimization problem through the use of simulated evolution, i.e., "survival of the fittest" strategy. The fittest element survives and reproduces, while inferior elements perish slowly. The population thus evolves and "improves" from generation to generation. Fitness is measured by a predefined objective function, such as homogeneity, for example. A set of molecular weights—to be selected as the feature set—is denoted a chromosome. The objective of the genetic algorithm 410 is to select an optimal low-dimension 'chromosome' to represent the (high-dimension) spectrum. For example, the 'chromosome' may have a real vector of size 10, whereas the full spectrum may have a vector of close to 11,500 points. FIG. 6 shows the design and implementation of the supervised feature architecture.

The operation of the feature extraction module 400 when used with training data may be divided into two stages, a training stage 10 and production stage 20. During the training stage 10, the supervised genetic algorithm 410 determines the set of molecular weights (a 'chromosome') for optimal classification performance. The performance index for the 'chromosome' (the 'fitness') may be defined as the homogeneity of the cluster-set created by a hierarchical clustering algorithm during the evolution of the 'chromosome'. In other words, the training set may be partitioned into K clusters, based on the features represented by the 'chromosome'. The homogeneity of the clusters, H(K), serves as the fitness of the 'chromosome' with higher being better. The training stage 10 may also be also used to design a neural network 520 of the classification module 500, as described more fully below. In addition, the genetic algorithm 410 may operate in tandem with a neural network 520 which functions as the classification module 500.

At the training stage 10, the genetic algorithm 410 is used to design the bestfeature extraction module 400 for each of the regularization modules A-H of FIG. 4. The time needed for the genetic algorithm 410 to complete its search for the optimal 'chromosome' is an indicator of the effectiveness of a particular regularization module 300, based on the assumption that better regularization would make the feature selection quicker. For example, in the present embodiment, the roulette wheel natural selection technique is used. In addition, to ensure that the fittest 'parents' would never be disqualified, the parents are preserved to the next generation without modification (using the elitist model).

During the production stage 20, the feature extraction module 400 selects the molecular weights that were determined to be optimal by the genetic algorithm 410 during the training stage 10.

Classification Module

After operation of the feature extraction module 400, the vector of extracted features, i. e., the spectra of selected molecular weights, is presented to the classification module 500 to group the spectra into subsets (clusters). A polypeptide spectrum in a cluster is supposed to be much 'closer' to other spectra in the same cluster than to those placed in another cluster.

The k-th cluster is denoted $X_k = \{\tilde{A}_{g,n}\}$, where $n \in \{n_1, n_2, \ldots, n_N\}$ is the set of N spectra included in the cluster; and $k \in \{1, 2, \ldots, K\}$, where K is the total number of clusters. The centroid of the k-th cluster $(\overline{X}_k)$ is defined to be $$\overline{X}_k = \frac{1}{N}\sum_{i=1}^{N} \tilde{A}_{g,n_i}.$$

A good clustering algorithm would have high intra-cluster similarity (homogeneity) and high inter-cluster dissimilarity (heterogeneity).

The classification module 500 may be an unsupervised classifier when no training data is available or may be a supervised classifier which makes use of training data. For an unsupervised classification module 500 a hierarchical clustering algorithm 510 may be used with the squared Euclidean distance as a metric. The hierarchical clustering algorithm 510 may be used to provide a distance measure to transform a set of data into a sequence ofnested partitions, a dendrogram. A dendrogram shows how the spectra are grouped in each step of clustering. The hierarchical clustering algorithm 510 may use agglomerative hierarchical clustering which may be particularly desirable due to its computational advantages. In agglomerative hierarchical clustering the number of clusters decreases towards the "root" of the dendrogram while the similarity between clusters increases, with the root of the dendrogram corresponds to the trivial, single cluster case.

A principal step in the agglomerative clustering is to merge two clusters that are the "closest" to each other. The distance between cluster r and s may be calculated by any suitable means, such as by using the average linkage $$d_c(X_r, X_s) = \frac{1}{N_r N_s}\sum_{i=1}^{N_r}\sum_{j=1}^{N_s}\sqrt{(\tilde{A}_{p,n_i} - \tilde{A}_{q,n_j})^2}, \quad (18)$$

where $N_r$ and $N_s$ are the numbers of spectra inside clusters $X_r$ and $X_s$ respectively.

Alternatively, the classification module 500 may include a neural network, such as a multi-layer, graded response multiperceptron neural network 520, for use when training data are available. A multi-layer graded response multiperceptron is a supervised-learning neural network that can realize a large family of nonlinear discriminant functions. One of the advantages of a neural network 520 is that once the neural network classification module 500 is trained, the computational requirements during the production stage 20 are low.

Another advantage is that an explicit model of the data is not needed, as the neural network 520 creates its own representation during training.

The multi-layer graded-response multiperceptron neural network 520 performs two roles. When unsupervised techniques are used, the multiperceptron neural network 520 is used to learn the true classification of the data from the output of the regularization and feature extraction modules 300, 400. When supervised techniques are used, the multiperceptron is trained at the training stage 10 (using known, labeled samples during the training stage) to fumction as the classification module 500 for the features extracted during the production stage 20.

The multiperceptron neural network 520 may include a three-layer network, which includes an input layer, a hidden layer, and an output layer. A tanh-sigmoid transfer function ($\phi(v)=\tan h(\alpha v)$) or a log-sigmoid transfer function ($\phi(v)=1/1+\exp(-\alpha v)$) is associated with each neuron, where "a" is the slope parameter which determines the slope of the transfer function, and "v" is the input to the neuron. The networks may be trained by the 'Resilient back-PROP agation' (RPROP) algorithm to recognize a certain classes of patterns.

The output from the classification module 500 provides the desired classification of input protein spectra. Consequently, the classification process is complete after operation by the classification module 500. However, it may be desirable to optionally include a validation module 600 for validating the classification. In particular, with reference to the examples below, the validation module 600 can provide insight into which of the regularization modules A-H produces more favorable results.

Validation Module

In the validation module 600, the homogeneity of the cluster set, and to a lesser extent the heterogeneity, may be used as criteria by which the effectiveness of the different regularization modules 300 A-H within the classifier architecture is evaluated. The performance may be assessed through criteria such as homogeneity and heterogeneity, computational speed, and, in the case of medical classification, the sensitivity and specificity of the classification results.

Homogeneity and heterogeneity are two descriptors particularly suited for assessment of clustering results. Homogeneity measures the average intra-cluster similarity. Homogeneity is a function of the number of formed clusters (K) and often tends to increase with K. Let $N_{total}$ be the total number of samples, and $J_k$ be the number of samples in the dominant group of $x_k$. Homogeneity is defined as $$H(K) = \frac{\sum_{k=1}^{K} J_k}{N_{total}}. \quad (19)$$

Heterogeneity measures the average inter-cluster dissimilarity. It uses the dispersion of centroids, given by $$H_e(K) = \left(\frac{1}{D_{max}}\right)\frac{1}{K^2}\sum_{j=1}^{K}\sum_{k=1}^{K}(\overline{X}_k - \overline{X}_j)^2, \quad (20)$$

where $D_{max}$ is the maximum distance between any two clusters.

The homogeneity index is considered more important than heterogeneity index, because heterogeneity does not take into account the accuracy of the classification result (as compared to the ground truth). Usually, the heterogeneity index is used in performance assessment only in order to differentiate classification results of similar homogeneity values.

The convergence time of the multiperceptron serves to assess the effectiveness of the regularization module 300.

C. Natural Grouping (Finding the Optimal Number of Clusters)

The statistical problem of finding the "natural grouping" (or determine "cluster validity") is ill posed. An "automated" method for cluster estimation by using the "gap statistic" was proposed by Tibshirani et al., "Estimating the number of clusters in a dataset via the gap statistic," *Tech. rep.* 208, Dept. of Statistics, Stanford University, 2000, the contents of which are incorporated herein by reference. This technique compares the change in an error measure (such as inner cluster dispersion) to that expected under an appropriate reference null distribution. During the division into natural clusters, an "elbow" usually occurs at the inner cluster dispersion function. The "gap statistic" tries to detect such elbows systematically. The maximum value of a gap curve should occur when the number of clusters corresponds to the natural grouping. However, on a real data, the gap curve often has several local maxima, and each local maximum can be informative, corresponding to a natural grouping. In that case of multiple maxima, the natural grouping is usually chosen that corresponds to the smallest number of clusters created, or consult additional criteria (such as heterogeneity).

EXAMPLES

In addition to model-based arguments, performance assessment was performed using two sets of real polypeptide spectra. These came from a 48 rat liver sample set subject to four toxicological conditions and a 199 ovarian cancer serum samples from diseased individuals and a control group.

The regularization modules A-H were compared and assessed using the two sets of real polypeptide spectrum data. One of the proposed modules demonstrated the best performance in terms of homogeneity of the clustering result, classification accuracy, and processing speed. This module, which was designed on the basis of the mathematical model, removed common characteristic and noise before it normalized the spectrum, and used the standard deviation as the normalization criterion. Removal of common characteristics and noise by this module made use of ensemble statistics of the spectrum set.

Example 1

The 48 rat liver samples were used to assess performance of the unsupervised classifier (FIG. 5) using the eight regularization modules 300 in FIG. 4. Performance was evaluated end-to-end through the homogeneity and heterogeneity of the clusters created by the classifier using hierarchical clustering. In addition, a neural network classifier was used (graded response multiperceptron) which was trained on the output of the feature extraction module 400 to memorize the correct classification of the data. The convergence speed of this neural network was another performance index for the system. The assumption was that better regularization would lead to better separation of the 'correct' clusters. Clusters that were well separated were easier to memorize by the neural network.

Homogeneity may be used to determine the appropriate number of clusters, K, where the hierarchical clustering algorithm should stop. In particular, a technique based on the "gap statistic" was used for this purpose.

Forty-eight polypeptide spectra were prepared from rat liver samples under four toxicological conditions (G=4). The sample preparation conditions are given in Table I.

TABLE I

Toxicological Conditions of 48 Rat Liver Samples

| Condition/ Group (g) | Treatment | Selection Criteria (visual inspection and ALT measurement) | Number samples chosen | Number of rats | Toxicity |
|---|---|---|---|---|---|
| Group 1 | Control | — | 18 | 2 | None |
| Group 2 | Alpha-naphthyl Isothiocyanate (ANIT) | Low-level hepatotoxicities | 12 | 2 | Mild |
| Group 3 | Carbon Tetrachloride (CCl4) | Low-level hepatotoxicities | 12 | 2 | Mild |
| Group 4 | Acetaminophen (APAP) | Visible liver lesions | 6 | 1 | High |

If liver cell protein expression were correlated to hepatotoxicity, the spectra should have formed clusters that were correlated to the four different treatments. While it was desirable that samples from each group be completely separated from those of other groups, it was especially important that samples from Group 4 (high toxicity) were separated from the others.

The 48 samples were placed onto six hydrophobic Protein-Chips in random order such that each chip had samples from at least three groups. The chips were divided into dtree batches and run through the ProteinChip biology system on three different days, to obtain 48 raw polypeptide spectra. Nine (9) samples were randomly chosen from the control group to be used in the ensemble variance analysis for common characteristic removal. The remaining 36 samples from the four (4) groups constituted the test set.

Inspection of the collected spectra revealed that meaningful data for classifications occurred only between 1.25 to 20 kDa. Therefore the spectra were presented to the preprocessing module 200 in that range. Each preprocessed polypeptide spectrum consisted of 11469 data points. All eight different regularization modules 300 A-H were then applied to the spectra to obtain eight different sets of normalized (and with modules C-H, compressed) spectra. For modules C-H, the common characteristics to be removed were identified using the nine (9) control group samples.

Figure 7A:
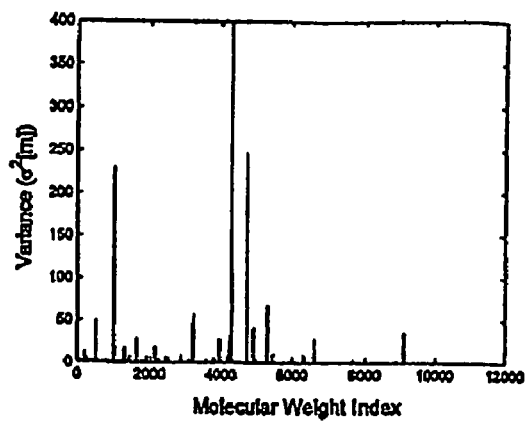
FIG. 7A illustrates a variance plot of the un-normalized control samples used in a first example of the present invention.

To illustrate the process, a description is provided of the two variance analyses for Modules D, G and H. The variance plots of the (un-normalized) control samples are shown in FIG. 7A. The ensemble variance $\sigma^2[m]$ included a few strong peaks, which corresponded to significant values of $var(\alpha_n[m]C[m])$. The noise floor corresponded to $var(N_n[m])$, and insignificant values of $var(\alpha_n[m]C[m])$. $\lambda=0.05$ was used in (4) to determine the molecular weights to be removed.

Figure 7B:
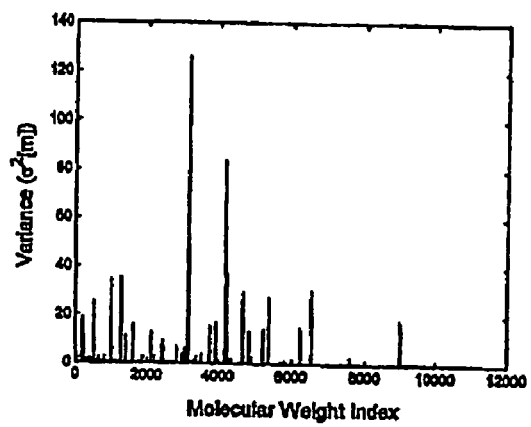
FIG. 7B illustrates the variance of the samples of FIG. 7A after common characteristic reduction was performed.
Figure 7C:
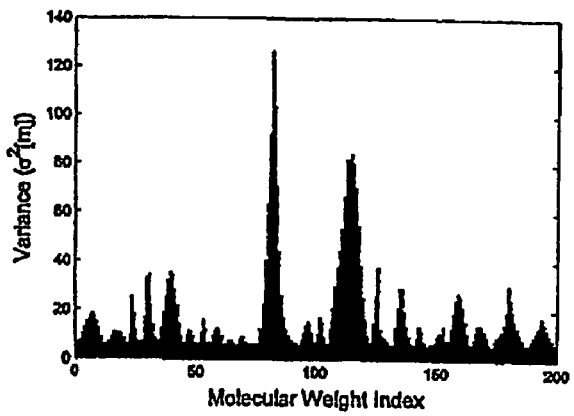
FIG. 7C illustrates the variance of the samples of FIG. 7B after molecular weights having relatively small variances were removed.
Figure 8A:
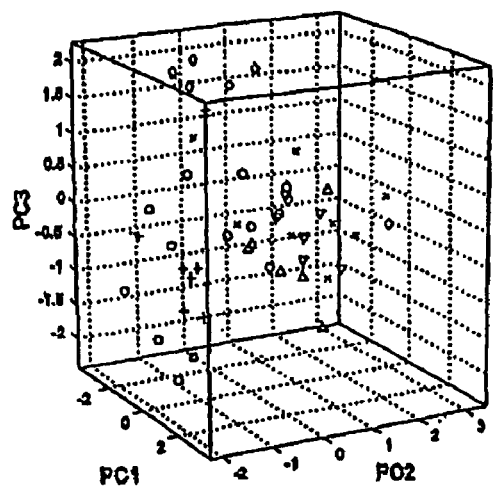
Figure 8B:
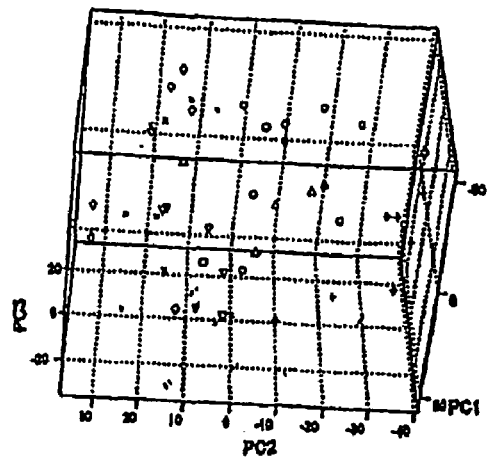
Figure 8C:
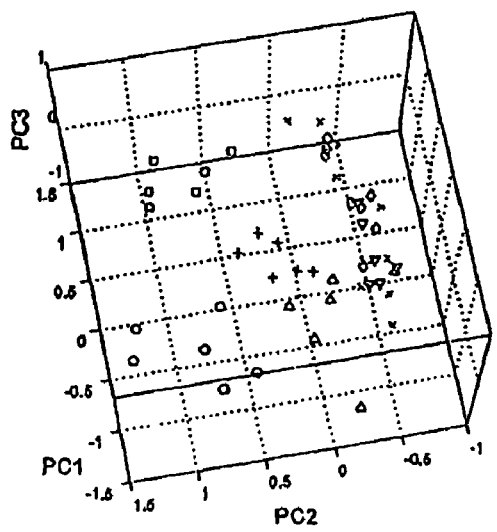
Figure 8D:
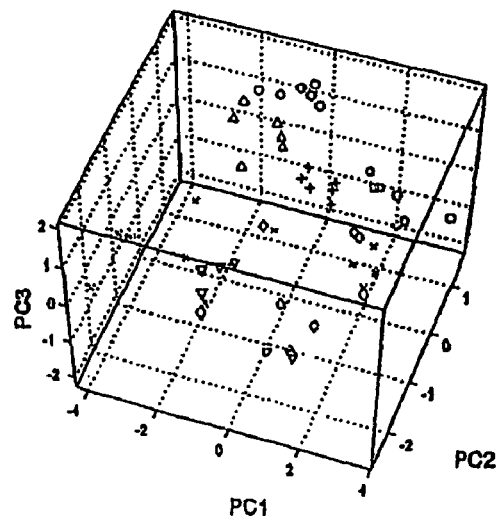
Figure 8F:
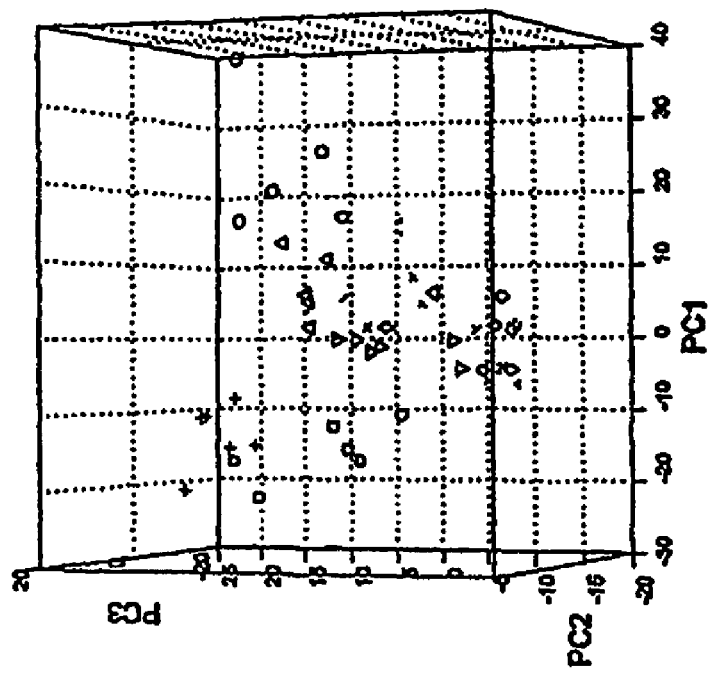
Figure 8E:
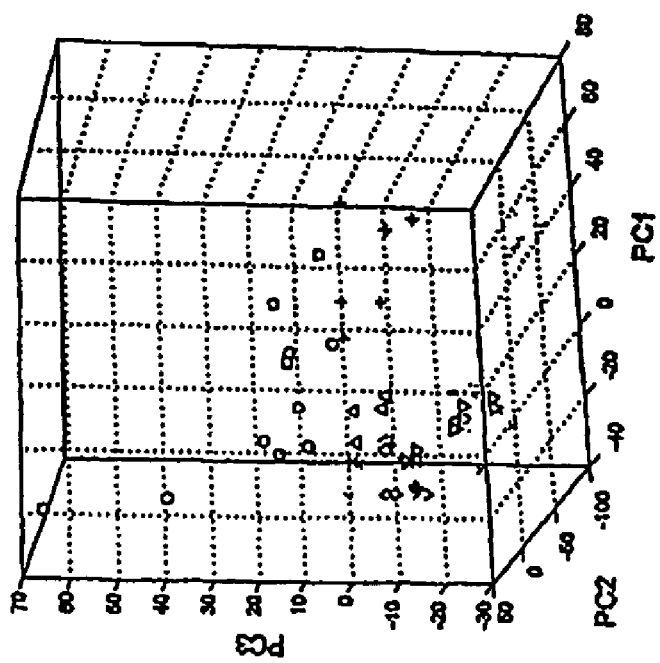

After common characteristic reduction, the variance of all forty-eight samples was considered (FIG. 7B). The plot includes a few peaks, which correspond to the significant values of $var(\alpha_n[m]A_g[m])$. Several molecular weights now exhibited strong intensities, which were not apparent in the variance plot of the control group (FIG. 7A). These might have corresponded to useful interclass discriminators and were retained. Again a threshold (4) with $\lambda=0.05$ was used to remove molecular weights that had relatively small variances. The variance plot of the final feature set is shown in FIG. 7C. The cardinarty of the feature set was greatly reduced (from about 11,500 to about 200) during this removal process.

The cardinalities of the retained feature sets for all regularization modules 300 are listed in Table II. The cardinality of module H (random feature selector) was chosen to match that of module G.

TABLE II

Cardinality of Feature Set Retained For Each Regularization Module

| Module | Feature Size |
|---|---|
| A | 11469 |
| B | 11469 |
| C | 185 |
| D | 199 |
| E | 106 |
| F | 80 |
| G | 199 |
| H | 199 |

The plots of the first three principal components for all eight modules are shown in FIGS. 8A-8I. All the plots are shown in viewing angles that exhibit visually the "best" separation between groups. For module H, only the first randomly selected feature set (out of 200 that were studied) is shown. In general, spectra from the same animal are closer to each other, which was to be expected. In addition, plots from modules C, E, F and G seem to have a better organization with respect to groups. Still, samples from Group 3 mix with samples from Group 1 occasionally. This was not completely unexpected, as Group 3 was "mildly toxic" and Group 1 was the control.

In order to decide on the number of features extracted by the PCA, the variance of each principal component was examined in every module (except for module H, where features were extracted at random). The cumulative percentages of total variability expressed by principal component (PC) 1 to 15 in modules A to G are listed in Table III. For each module (column in the table), the cumulative percentage in each row (PC) represents the percentage of total variability contributed by all principal components from PC1 up to that row. Principal components that expressed at least 90% of the total variability in each module were retained. The cumulative percentages of the retained principal components are listed in bold typeface in the table. The resulting extracted feature size is given in Table IV. The feature size for module H was chosen to match the feature size of module G.

TABLE III

Cumulative Percentage of Total Variability Explained by Principal Component 1-15 in Regularization Module A-G

| | Module | | | | | | |
|---|---|---|---|---|---|---|---|
| | A | B | C | D | E | F | G |
| PC1 | 32.71 | 33.97 | 34.08 | 36.57 | 33.59 | 37.42 | 34.42 |
| PC2 | 47.58 | 49.76 | 58.02 | 54.69 | 61.73 | 65.12 | 53.50 |
| PC3 | 58.58 | 59.92 | 71.15 | 66.09 | 80.70 | 81.38 | 67.28 |
| PC4 | 66.92 | 67.59 | 77.70 | 75.02 | 85.09 | 86.47 | 75.35 |
| PC5 | 72.57 | 74.83 | 83.43 | 80.23 | 88.87 | 90.76 | 80.03 |
| PC6 | 77.91 | 79.18 | 86.68 | 84.79 | 91.47 | 93.32 | 84.30 |
| PC7 | 81.85 | 82.40 | 89.49 | 88.49 | 93.77 | 95.35 | 87.72 |
| PC8 | 84.56 | 84.95 | 91.10 | 90.67 | 94.96 | 96.41 | 90.27 |
| PC9 | 86.90 | 87.31 | 92.62 | 92.10 | 95.96 | 97.06 | 91.88 |
| PC10 | 88.92 | 88.78 | 93.73 | 93.39 | 96.68 | 97.58 | 93.22 |

TABLE III-continued

Cumulative Percentage of Total Variability Explained by Principal Component 1-15 in Regularization Module A-G

| | Module | | | | | | |
|---|---|---|---|---|---|---|---|
| | A | B | C | D | E | F | G |
| PC11 | 90.28 | 90.13 | 94.72 | 94.49 | 97.34 | 98.01 | 94.30 |
| PC12 | 91.43 | 91.05 | 95.56 | 95.39 | 97.76 | 98.37 | 95.07 |
| PC13 | 92.29 | 91.81 | 96.24 | 96.05 | 98.15 | 98.71 | 95.81 |
| PC14 | 93.03 | 92.49 | 96.80 | 96.61 | 98.50 | 98.93 | 96.33 |
| PC15 | 93.60 | 93.08 | 97.19 | 97.13 | 98.73 | 99.12 | 96.83 |

TABLE IV

Cardinality of the Feature Set Retained After PCA

| | Module | | | | | | | |
|---|---|---|---|---|---|---|---|---|
| | A | B | C | D | E | F | G | H |
| Feature Size | 1 1 | 1 1 | 8 | 8 | 6 | 5 | 8 | 8 |

The eight feature sets provided by the feature extraction module 400 were clustered by the hierarchical clustering algorithm. A dendrogram was built for each feature set. Tables V-a and V-b show (respectively) the homogeneity and heterogeneity of each module versus K, the number of clusters formed (K ranges from 2 to 10). The mean and standard deviation for module H are also given.

The best performing module for each K is indicated in bold. As expected, the homogeneity index increases with K. Module G outperforms all other module for all K values larger than four (4). Not surprisingly the homogeneity of module G was always higher than that of module H (module H selects features at random, to match the cardinality of the feature set of module G). Considering module G, more than 98% of the spectrum data were filtered out by its common characteristic and noise removal stage 300. Yet, the highly homogeneous result shows that useful information was still preserved. As for heterogeneity, modules A and B have the highest values in most cases, followed by G. The combined scalar performance index (shown in Table V-c) was the sum of homogeneity and heterogeneity indices (the higher the index, the better the performance). This index was probably 'biased' in favor of heterogeneity, but even if the heterogeneity is discounted the final outcome remains the same.

The next task was to determine which row in table V-c (i.e., which value of K, the number of classes) should be used to compare the regularization modules 300. Table VI shows the gap statistics for K=2 to 10. The first local maxima after K=2 was listed in bold typeface. The optimal value of K, denoted K*, was chosen to be the average of the first local maxima of all regularization modules 300 (excluding Module D, which had no local maximum in the range 2-10), which was K*5. By referring back to Table V-c with K=5, module G had the best performance index, followed by modules E, B, and F.

TABLE V-a

Homogeneity Comparison between regularization modules 300

| | Module | | | | | | | |
|---|---|---|---|---|---|---|---|---|
| | A | B | C | D | E | F | G | H mean ± std. dev. |
| K = 2 | 0.4167 | 0.4167 | 0.5000 | 0.3750 | 0.3958 | 0.3958 | 0.4583 | 0.4251 ± 0.0595 |
| K = 3 | 0.4167 | 0.4792 | 0.5208 | 0.3750 | 0.5208 | 0.6458 | 0.4792 | 0.4872 ± 0.0881 |
| K = 4 | 0.4167 | 0.5625 | 0.6458 | 0.4792 | 0.7708 | 0.7500 | 0.6042 | 0.5246 ± 0.0936 |
| K = 5 | 0.4792 | 0.6042 | 0.7083 | 0.4792 | 0.7708 | 0.7500 | 0.8542 | 0.5540 ± 0.0934 |
| K = 6 | 0.5625 | 0.6458 | 0.8333 | 0.5417 | 0.7708 | 0.7500 | 0.8958 | 0.5801 ± 0.0932 |
| K = 7 | 0.6250 | 0.6458 | 0.8333 | 0.6042 | 0.8542 | 0.7917 | 0.8958 | 0.6038 ± 0.0933 |
| K = 8 | 0.7292 | 0.6458 | 0.8333 | 0.7292 | 0.8542 | 0.7917 | 0.8958 | 0.6268 ± 0.0922 |
| K = 9 | 0.7708 | 0.6667 | 0.8333 | 0.7708 | 0.8542 | 0.7917 | 0.8958 | 0.6464 ± 0.0901 |
| K = 10 | 0.7708 | 0.7292 | 0.8333 | 0.8958 | 0.8542 | 0.8333 | 0.8958 | 0.6664 ± 0.0884 |
| K = 2 | 0.5000 | 0.5000 | 0.5000 | 0.5000 | 0.5000 | 0.5000 | 0.5000 | 0.5000 ± 0.0000 |
| K = 3 | 0.5560 | 0.6273 | 0.6032 | 0.5169 | 0.5193 | 0.4181 | 0.5398 | 0.4883 ± 0.0734 |
| K = 4 | 0.5726 | 0.6442 | 0.4069 | 0.4241 | 0.4250 | 0.3479 | 0.5300 | 0.4455 ± 0.0816 |
| K = 5 | 0.5672 | 0.5975 | 0.3818 | 0.3972 | 0.4601 | 0.3460 | 0.4782 | 0.4327 ± 0.0714 |
| K = 6 | 0.5612 | 0.5178 | 0.3482 | 0.3762 | 0.3987 | 0.3204 | 0.5170 | 0.4217 ± 0.0630 |
| K = 7 | 0.5855 | 0.4663 | 0.3554 | 0.3177 | 0.3755 | 0.3084 | 0.5313 | 0.4127 ± 0.0622 |
| K = 8 | 0.5809 | 0.4884 | 0.3808 | 0.3001 | 0.3817 | 0.2913 | 0.5362 | 0.4042 ± 0.0581 |
| K = 9 | 0.4325 | 0.5103 | 0.3558 | 0.2982 | 0.3660 | 0.2879 | 0.4458 | 0.4006 ± 0.0571 |
| K = 10 | 0.3595 | 0.4564 | 0.3574 | 0.2858 | 0.3743 | 0.2704 | 0.4760 | 0.3912 ± 0.0537 |

TABLE V-c

Performance Index Comparison between regularization modules 300

| | Module | | | | | | | |
|---|---|---|---|---|---|---|---|---|
| | A | B | C | D | E | F | G | H (mean) |
| K = 2 | 0.9167 | 0.9167 | 1.0000 | 0.8750 | 0.8958 | 0.8958 | 0.9583 | 0.9251 |
| K = 3 | 0.9727 | 1.1065 | 1.1241 | 0.8919 | 1.0402 | 1.0640 | 1.0190 | 0.9754 |
| K = 4 | 0.9892 | 1.2067 | 1.0527 | 0.9033 | 1.1959 | 1.0979 | 1.1341 | 0.9700 |
| K = 5 | 1.0464 | 1.2016 | 1.0901 | 0.8764 | 1.2310 | 1.0960 | 1.3323 | 0.9866 |
| K = 6 | 1.1237 | 1.1637 | 1.1816 | 0.9179 | 1.1695 | 1.0704 | 1.4128 | 1.0018 |
| K = 7 | 1.2105 | 1.1121 | 1.1888 | 0.9218 | 1.2296 | 1.1000 | 1.4272 | 1.0164 |

TABLE V-c-continued

Performance Index Comparison between regularization modules 300

| | Module | | | | | | | |
|---|---|---|---|---|---|---|---|---|
| | A | B | C | D | E | F | G | H (mean) |
| K = 8 | 1.3101 | 1.1342 | 1.2142 | 1.0293 | 1.2358 | 1.0830 | 1.4320 | 1.0310 |
| K = 9 | 1.2034 | 1.1770 | 1.1892 | 1.0690 | 1.2202 | 1.0796 | 1.3417 | 1.0470 |
| K = 10 | 1.1304 | 1.1856 | 1.1907 | 1.1817 | 1.2285 | 1.1037 | 1.3718 | 1.0576 |

TABLE VI

Gap Statistics for the regularization modules 300

| | Module | | | | | | |
|---|---|---|---|---|---|---|---|
| | A | B | C | D | E | F | G |
| K = 2 | 0.2238 | 0.1241 | 0.0844 | 0.0937 | 0.1919 | 0.0420 | 0.1405 |
| K = 3 | 0.2177 | 0.1190 | 0.0388 | 0.0602 | 0.1878 | 0.1542 | 0.0921 |
| K = 4 | 0.1955 | 0.1176 | 0.1190 | 0.1690 | 0.3102 | 0.2359 | 0.1108 |
| K = 5 | 0.1875 | 0.1435 | 0.2014 | 0.1789 | 0.2762 | 0.2268 | 0.2025 |
| K = 6 | 0.2072 | 0.1927 | 0.2457 | 0.2319 | 0.2806 | 0.2113 | 0.1953 |
| K = 7 | 0.2102 | 0.2055 | 0.2323 | 0.2510 | 0.4034 | 0.3336 | 0.2384 |
| K = 8 | 0.2701 | 0.2081 | 0.2433 | 0.3296 | 0.3829 | 0.3401 | 0.2828 |
| K = 9 | 0.2878 | 0.2010 | 0.2444 | 0.3338 | 0.3969 | 0.3150 | 0.2800 |
| K = 10 | 0.2888 | 0.2294 | 0.2379 | 0.3823 | 0.3833 | 0.3539 | 0.2655 |

Figure 9A:
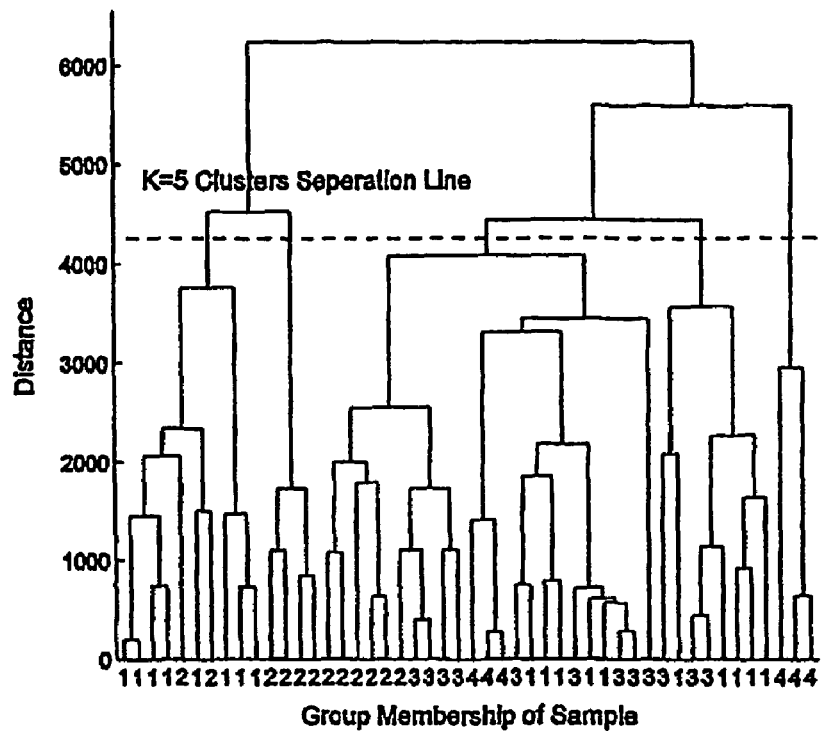
FIGS. 9A and 9B illustrate dendrograms showing the performance of two of the regularization module with module B and module G of FIG. 4, respectively.
Figure 9B:
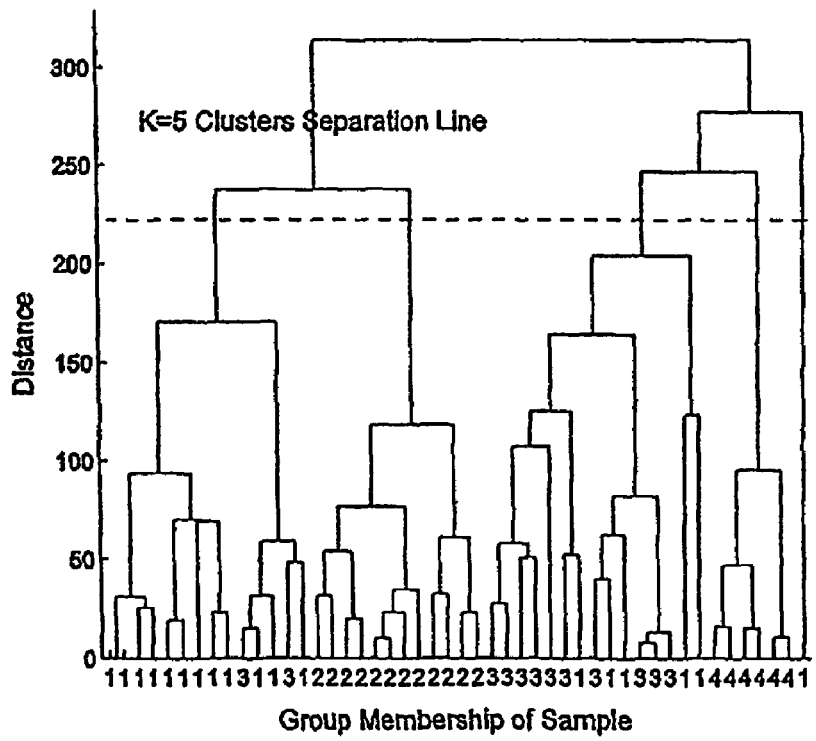

To illustrate the classification performance further, the dendrograms of two of the regularization modules 300, module B (FIG. 9A) and module G (FIG. 9B), are shown. The height of the dendrogram corresponds to the distance between clusters formed at each step. The horizontal axis provides the actual group membership of each sample. The dotted line in the figures was the "separation line" for the five clusters. The dendrogram of module G was preferred, as it was separated naturally into five clusters (with one cluster consisting of a possible outlier). The natural separation of module B's dendrogram was less clear-cut (it has low heterogeneity). These dendrograms demonstrate how the addition of the filtering stage in the regularization module 300 (Path 1(c) in FIG. 1 improves classification.

Finally, Table VII presents the actual clustering results for Module G at K=5. The table provides the actual group memberships of samples from each cluster. Two out of the five clusters (namely, clusters 2 and 4) are 100% homogeneous. Technically so was cluster 5, but it only has one (1) member, and probably it represents an outlier. Most importantly, module G was able to separate Group 2 and Group 4 (the most toxic case) from the rest of the samples. As noted above, the intermixing of Group 1 and Group 3 in clusters 2 and 3 was not surprising, since Group 1 was the control group and Group 3 was the "mildly" toxic group. Cluster 5, which includes a single element, was an outlier. In the remaining four (4) clusters, each has a dominant number of samples from one of the four (4) groups. Most importantly, the results are consistent with the hepatoxicity of the samples.

TABLE VII

Classification Result Using Module G (K = 5)

| | Group 1 | Group 2 | Group 3 | Group 4 | subtotal |
|---|---|---|---|---|---|
| Cluster 1 | 12 | 0 | 2 | 0 | 14 |
| Cluster 2 | 0 | 12 | 0 | 0 | 12 |
| Cluster 3 | 5 | 0 | 10 | 0 | 15 |
| Cluster 4 | 0 | 0 | 0 | 6 | 6 |
| Cluster 5* | 1 | 0 | 0 | 0 | 1 |
| Subtotal | 18 | 12 | 12 | 6 | 48 |

*Cluster 5 was a potential outlier cluster.

The feature sets from Modules A-G were presented to 3-layer multiperceptron networks 520. These were trrrned through the RPROP algorithm to fit the correct labels. Module H was dropped at this stage since it was shown to be inferior to module G in the last section. The input layer of the network had the same number of neurons as the cardinality of the feature set under testing. The middle layer was set to have 40 neurons and the output layer had 4 neurons. The targeted outputs were [1 0 0 0], [0 1 0 0], [0 0 1 0], and [0 0 0 1]. Each output corresponded to a single group of spectra.

In this evaluation, in the convergence speed of the multilayer neural network, i.e. the computational time needed for a network to memorize the correct classification of all the presented proteomic patterns, was used to measure the performance of the network. The correctness was measured by the mean square error (MSE) between the actual and the targeted output. In the tests, the stopping criterion was an MSE of 0.001. Since the convergence speed might have depended on network initialization, 500 random network initializations were used to determine the average convergence time and its standard deviation for each regularization module 300.

The convergence time results are shown in Table VI. The convergence speed was related to the proximity of the spectra in the feature space. As shown in Table VIII, modules B and G are the 'winners'. Given the difference in size between the data sets that these techniques employ (11469 for B, 199 for G) Module G continues to be preferred.

TABLE VIII

| | | \multicolumn{7}{c}{Convergence Time for Multi-Perceptron Network} |
| | | \multicolumn{7}{c}{Module} |
| | | A | B | C | D | E | F | G |
|---|---|---|---|---|---|---|---|---|
| Epoch to Converge | Average | 21.2340 | 17.2340 | 27.2100 | 20.8460 | 24.2840 | 21.6580 | 18.0800 |
| | Std. Dev. | 3.5168 | 4.6711 | 4.5628 | 4.3787 | 5.8109 | 4.2715 | 3.7026 |

It was concluded that module G had the best performance, followed by modules B, E and F. Out of these four modules, three (B, F, and G) used normalization to the standard deviation. In Example 2, only modules A, B, F, and G were used. Module E was dropped, since it was unable to process certain artifacts.

Example 2

Performance Evaluation Using 199 Serum Samples (2 Groups)

The second data set was used to design and test a supervised classifier (FIG. 6). This set consisted of 199 spectra from the Clinical Proteomics.Program Databank of the National Institutes of Health (NIH)/Food and Drug Administration (FDA). The design of the classifier was performed during the training stage 10 and the performance was evaluated during a production stage 20. In the training stage 10, a supervised genetic algorithm was coupled with the regularization module 300 to determine the optimum set of molecular weights that separate the samples to 'diseased' and 'unaffected'. The traning stage 10 was further divided into (1) a learning phase, during which a group of prospective neural networks was created; and (2) a selection phase, during which the best of these networks was selected from the group for the production stage. For the learning phase, 100 serum samples were used (training set I—50 'diseased' and 50 'unaffected' samples). For the selection phase, another 20 serum samples were used (training set II—10 'diseased' and 10 'unaffected' samples).

During the production stage, a new set of 79 samples (40 'diseased' and 39 'unaffected' samples) was presented to the system. The best neural network (from the selection phase) was used to decide on the group membership of each sample ('diseased' or 'unaffected'). Finally, the quality of the decision was assessed by comparison to the ground truth. Parameters of interest included classification accuracy and computational speed.

The 199 spectra were prepared by NIH/FDA using WCX2 chips. The 16 benign disease cases were not used ("s-01 modified" to "s-16 modified"). One control sample ("d-49 modified") was found to be duplicated and was discarded as well. The data set consisted of 99 ('unaffected') control samples and 100 ('diseased') ovarian cancer samples. A detailed description of the sample collection methodology can be found in E. F. III Petricoin, A. M. Ardekani, B. A. Hitt et al., "Use of proteomic patterns in serum to identify ovarian cancer," Lancet 359:572-77, 2002 (Petricoin), the contents of which are incorporated herein by reference. The data set used in Petricoin was collected using H4 chip, and had a slightly different composition than the dataset (Apr. 3, 2002) from the NIH/FDA. However the data sampling and collection methods were similar. Fifty (50) 'diseased' and fifty (50) 'unaffected' samples were selected randomly as training set I (for network learning). Another ten (10) samples of each kind were selected randomly to be training set II (for network selection). The rest of the samples were used for performance evaluation.

Figure 10:
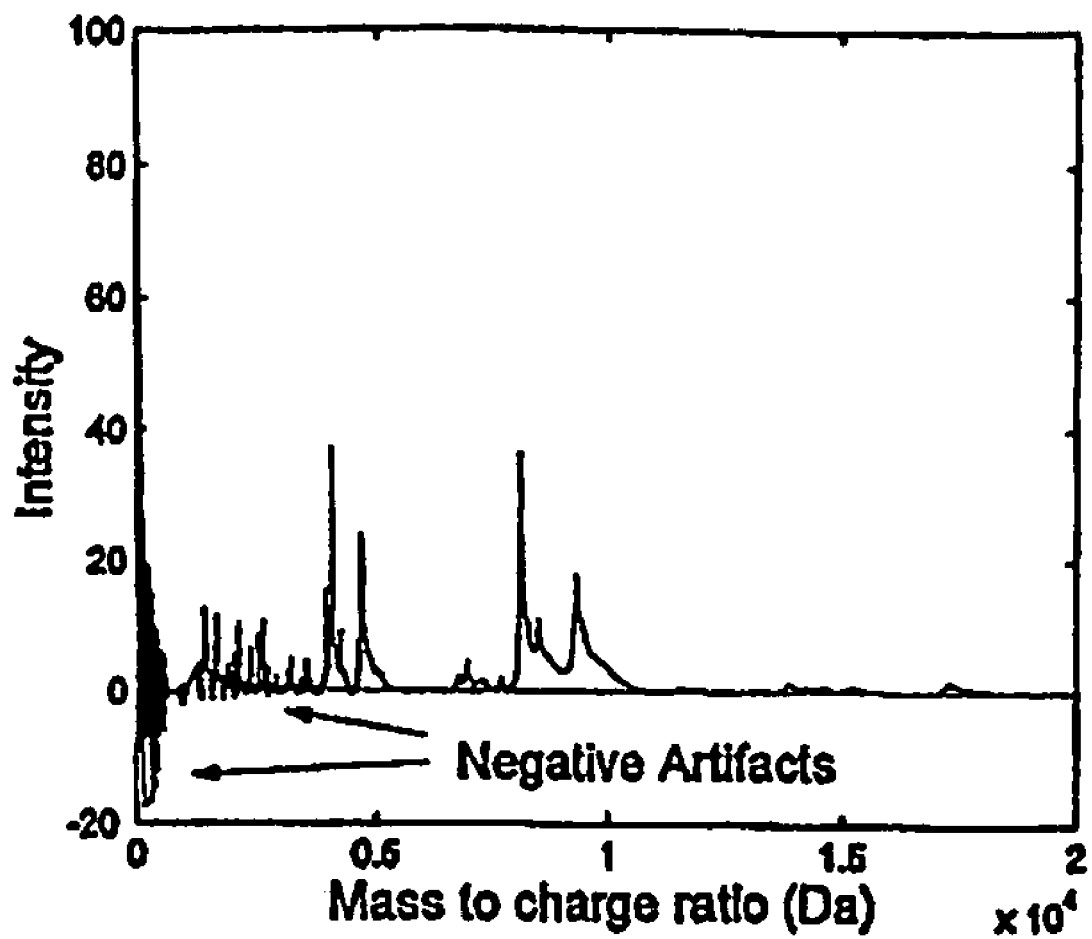
FIG. 10 illustrates an exemplary spectrum from the data set of the second example with baseline subtraction.

The data were provided after the baseline was subtracted using Ciphergen's software. The process seemed to have created artifacts such as negative values for the spectrum (as large as −30) around the 4 kDa section as seen in FIG. 10. These artifacts added a challenge to the classifier operation and excluded the use of total ion current normalization (Module E) in this part of the experiment. As indicated above, only Modules A, B, F and G were considered (C, D, and H were inferior and E was inapplicable).

To avoid the low-weight noisy region the maximum value needed for normalization in module A was determined from intensity of molecular weights larger than 800 Da For modules F and G, a threshold of the form (4) witht $\lambda=0.05$, was used for the variance analysis in the common characteristic removal stage. $\lambda=0.01$ was used for the variance analysis in the noise removal stage. The cardinality of the feature set for each module is shown in Table X. Clearly, Modules F and G have a size advantage.

TABLE X

Feature Size of the Selected regularization modules 300

| Module | Feature Size |
|---|---|
| A | 15154 |
| B | 15154 |
| F | 6407 |
| G | 6277 |

During the training stage 10 a supervised genetic algorithm (genetic algorithm 410) determined the optimum set of molecular weights (the 'chromosome') that separated the 'diseased' and 'unaffected' samples. It used 100 training samples. The "chromosome size" was chosen to be ten (10) molecular weights. (Thus, the dimension of the solution space was D=10.) The dimension of the search domain was the number of points retained after regularization. The genetic algorithm 410 began the preprocessing with a population of 1000 'chromosomes,' chosen pseudo-randomly from the search domain During each iteration, a new generation of 1000 'chromosomes' was generated by crossover or mutation, according to the fitness of their predecessors. The fitness of a 'chromosome' was determined by the following test. First the training spectra (represented by the D features of their 'chromosome') were partitioned to K clusters using unsupervised hierarchical clustering in the D-dimensional space. (The value of K was selected to be larger than the number of groups, G=2, to account for possible outliers; a value of K=10 was chosen). Each 'chromosome' was then assigned a fitness value equal to the homogeneity H(K) of the clusters that it had induced.

The mutation rate was 0.02%. The genetic algorithm 410 iterated for 300 generations or until the optimum chromosome, which gave H(10)=1, was found. The performance of the genetic algorithm 410 was measured through the computational time needed to find the optimum chromosome.

At this point the ten (10) molecular weights which corresponded to the best 'chromosome' were known. A 10-tuple comprised of values of this spectrum at these ten (10) molecular weights was extracted from each spectrum. Next, a neural network task was designed that would classify the 10-tuples correctly. It was accomplished by training, showing the network an input (a 10-tuple representing the spectrum) and a corresponding 'target'. The target was "1" for inputs corresponding to 'diseased' samples, and "−1" for inputs corresponding to 'unaffected' cases. 3000 different random weight initialization of the network was used, resulting in 3000 distinct neural networks. The convergence time and standard deviation for each module were measured; if a network did not converge after 2000 epochs, the session was abandoned.

A second set of new twenty (20) 10-tuple training samples was used to measure classification accuracies of the 3000 trained neural networks. The network with the best accuracy (or in case of tie, fastest convergence time among the tied contenders) was selected for the production stage.

During the production stage, 79 new spectra were used to assess end-to-end performance of the classifier. Performance was compared using different regularization modules 300 and used classification accuracy as the performance index.

Figure 11:
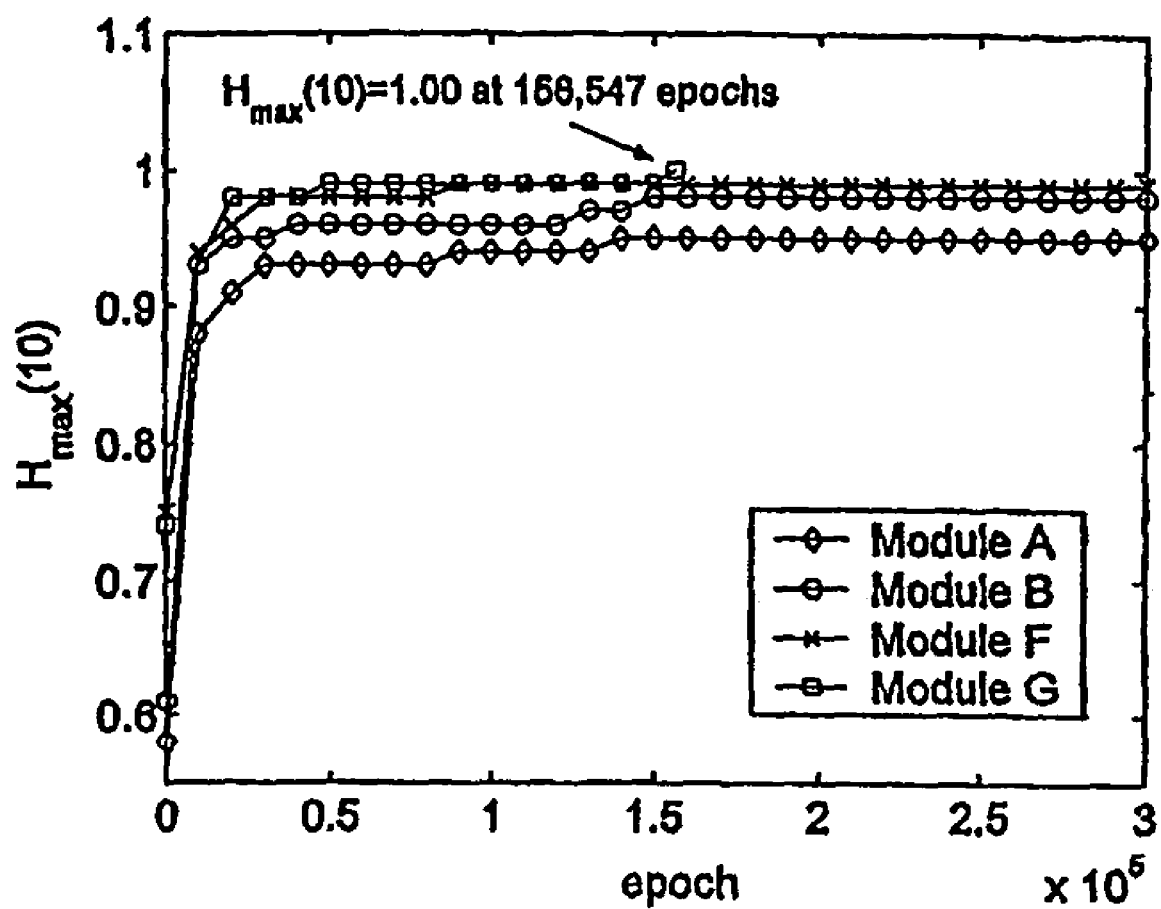
FIG. 11 schematically illustrates the homogeneity of the best chromosome found at each epoch after pattern recognition in example 2.

FIG. 11 shows the homogeneity of the best chromosome found at each epoch (an epoch was the computational time unit needed to run one fitness test). Modules A, B and F were unable to obtain perfect homogenous clusters when the algorithm was stopped, after 300,000 epochs. Module G was able to yield perfect homogenous clusters after 156,547 epochs. The convergence of module G is therefore attributed to its better regularization. It was also observed that modules G and F, which used filtering in addition to normalization, had higher final homogeneity values compared to the "normalization only" modules, A and B. Also, modules B, F and G, which used normalization to standard deviation, had higher final homogeneity values than module A, which used normalization to maximum.

Table X compares convergence of the neural networks for the three modules. Module G has the lowest percentage of non-convergent networks and the best convergence time of the convergent networks (though modules B and F are strong contenders). The standard deviation was high, since some networks in each case took quite a long time to converge.

Again, the modules with additional removal inside the regularization module 300 performed better than those with "normalization only" modules. Modules that normalized to standard deviation were better than those that normalized to maximum.

TABLE X

Convergence time for neural networks training

| Module | Percentage do not converge | Computational time to convergence for those converge (Epoch) | |
|---|---|---|---|
| | | Average | Standard Deviation |
| A | 4.33% | 52.96 | 157.86 |
| B | 0.90% | 54.19 | 150.60 |
| F | 0.70% | 39.85 | 105.57 |
| G | 0.17% | 34.68 | 111.02 |

Table XI shows the classification results using each one of the modules. There were 40 'diseased' samples taken from women who had ovarian cancer; column (1) shows how many of those were classified as 'diseased' and how many are 'unaffected'. There were 39 'unaffected' samples, and column (2) shows how many of them were classified as 'diseased' and how many 'unaffected'. The sensitivity (column 3) and specificity (column 4) are also shown for each classifier. From these data, it is concluded that the classifier that employed module G provides the best results.

TABLE XI

Classification results - 79 serum sample set

| | | Women with ovarian cancer (1) | Unaffected Women (2) | Sensitivity (3) | Specificity (4) |
|---|---|---|---|---|---|
| Module A | Diseased | 36/40 | 3/39 | 90.00% | 92.31% |
| | Unaffected | 4/40 | 36/39 | | |
| Module B | Diseased | 35/40 | 4/39 | 87.50% | 89.74% |
| | Unaffected | 5/40 | 35/39 | | |
| Module F | Diseased | 36/40 | 2/39 | 90.00% | 94.87% |
| | Unaffected | 4/40 | 37/39 | | |
| Module G | Diseased | 39/40 | 2/39 | 97.50% | 94.87% |
| | Unaffected | 1/40 | 37/39 | | |

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention was not limited to the particular embodiments described herein, but was intended to include all changes and modifications that are within the scope and spirit of the invention as set forth in the claims.

Symbol Table

| Symbol | Meaning |
|---|---|
| $\alpha_n$ | experiment-dependent attenuation coefficient |
| a | slope parameter of neural network transfer function |
| $A_g[m]$ | additive polypeptide response of interest due to a condition-g |
| $A_{g,n}[m]$ | observed polypeptide spectrum during the $n^{th}$ experiment |
| $\tilde{A}_{g,n}$ | normalized observed polypeptide spectrum |
| $\beta$ | constant average ion current |
| $B_g[m]$ | summation of $A_g[m]$ and constant portion of $C[m]$ |
| $C[m]$ | common characteristic |
| $\Delta A$ | scaled expected distance between polypeptide response of interest |
| $\Delta C$ | scaled expected distance between common characteristic |
| $\Delta D$ | expected distance between measured spectra |
| $\Delta N$ | expected distance between noise |
| $d_c(X_r, X_s)$ | average distance between spectra from cluster $X_r$ and $X_s$ |
| $D_{max}$ | maximum inter-centroid distance |
| g, p, q | label for pathological or toxicological condition |
| G | number of conditions |
| H(K) | homogeneity index |
| $H_e(K)$ | heterogeneity index |
| $\bar{I}_n$ | average ion current |
| $J_k$ | number of samples in the dominant group of $X_k$ |
| k | label for cluster of normalized spectra |
| K | number of clusters |
| $\lambda$ | fractional coefficient used to calculate filter threshold |
| m | molecular weight |
| M | Total number of molecular weights |
| $\mu_n$ | mean of a spectrum |
| n, i, j | label for experiment |
| N | number of spectra |
| $N_n[m]$ | additive noise term introduced by the experiment |
| $\phi(v)$ | neural network transfer function |
| $\sigma^2$ | variance of a spectrum |
| v | input to neural network transfer function |
| var( ) | variance operator |

-continued

| Symbol | Meaning |
|---|---|
| $X_k$ | k-th cluster of normalized spectra |
| $\overline{X}_k$ | centroid of the k-th cluster |

What is claimed is:

1. A data analyzer for use with a pattern classifier to compress a set of indexed data having common characteristics and noise, comprising:
   a. means for determining a common characteristic threshold for the indexed data set;
   b. means for removing indices having an ensemble statistic higher than the common characteristic threshold value in order to provide a retained dataset, wherein the ensemble statistic is a statistic taken from across a set of spectra;
   c. means for calculating the ensemble statistic of each retained index in the retained dataset;
   d. means for determining a noise threshold;
   e. means for removing indices from the retained dataset wherein the ensemble statistic is lower than a noise threshold value; and
   f. means for normalizing the indexed data.

2. The data analyzer according to claim 1, wherein the normalization means is configured to process the indexed data prior to processing by the common characteristic threshold means.

3. The data analyzer according to claim 1, wherein the normalization means is configured to process the indexed data after processing by the common characteristic threshold means.

4. The data analyzer according to claim 1, wherein the normalization means comprises means for normalizing a member of the set to the standard deviation of the member.

5. The data analyzer according to claim 1, wherein the normalization means comprises means for normalizing a member of the set to the maximum value of the member.

6. A method for classifying a set of indexed data that includes obtaining a collection of control spectra obtained via mass spectrometry, comprising the steps of:
   a. calculating an ensemble statistic at each index in the control spectra obtained via mass spectrometry, wherein the ensemble statistic is a statistic taken from across a set of spectra;
   b. identifying those indices at which the ensemble statistic exceeds a first selected threshold;
   c. removing the identified indices from all spectra in the set of indexed data to provide a set of compressed indexed data;
   d. calculating an ensemble statistic at each index of the compressed indexed data;
   e. removing all indices from each compressed spectrum that have an ensemble statistic that is lower than a second selected threshold value to provide a set of reduced indexed data;
   f. extracting a feature portion of each of the reduced indexed data to provide a set of feature spectra;
   g. classifying the set of feature spectra into clusters; and
      wherein the step of calculating the ensemble statistic at each index in the control spectra comprises computing an ensemble variance of the control spectra.

7. A method for classifying a set of indexed data that includes obtaining a set of control spectra obtained via mass spectrometry, comprising the steps of:
   a. calculating an ensemble statistic at each index in the control spectra obtained via mass spectrometry, wherein the ensemble statistic is a statistic taken from across a set of spectra;
   b. identifying those indices at which the ensemble statistic exceeds a first selected threshold;
   c. removing the identified indices from all spectra in the set of indexed data to provide a set of compressed indexed data;
   d. calculating an ensemble statistic at each index of the compressed indexed data;
   e. removing all indices from each compressed spectrum that have an ensemble statistic that is lower than a second selected threshold value to provide a set of reduced indexed data;
   f. extracting a feature portion of each of the reduced indexed data to provide a set of feature spectra;
   g. classifying the set of feature spectra into clusters; and
      wherein the step of calculating the ensemble statistic at each index of the compressed indexed data comprises computing an ensemble variance of the compressed indexed data.

* * * * *